(12) United States Patent
Fujii et al.

(10) Patent No.: US 9,347,873 B2
(45) Date of Patent: May 24, 2016

(54) IMAGE FORMING APPARATUS, CALIBRATION METHOD, AND DRYING DETERMINATION METHOD

(71) Applicants: Masayuki Fujii, Kanagawa (JP); Nobuyuki Satoh, Kanagawa (JP); Mamoru Yorimoto, Kanagawa (JP); Masato Kobayashi, Kanagawa (JP); Hiroshi Matsumoto, Kanagawa (JP); Daisaku Horikawa, Kanagawa (JP); Suguru Yokozawa, Kanagawa (JP); Kenji Morita, Tokyo (JP); Yuichi Sakurada, Tokyo (JP); Tomohiro Sasa, Kanagawa (JP); Masaya Kawarada, Kanagawa (JP)

(72) Inventors: Masayuki Fujii, Kanagawa (JP); Nobuyuki Satoh, Kanagawa (JP); Mamoru Yorimoto, Kanagawa (JP); Masato Kobayashi, Kanagawa (JP); Hiroshi Matsumoto, Kanagawa (JP); Daisaku Horikawa, Kanagawa (JP); Suguru Yokozawa, Kanagawa (JP); Kenji Morita, Tokyo (JP); Yuichi Sakurada, Tokyo (JP); Tomohiro Sasa, Kanagawa (JP); Masaya Kawarada, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/563,643

(22) Filed: Dec. 8, 2014

(65) Prior Publication Data

US 2015/0158309 A1    Jun. 11, 2015

(30) Foreign Application Priority Data

Dec. 9, 2013 (JP) .................................. 2013-254553
Dec. 1, 2014 (JP) .................................. 2014-243562

(51) Int. Cl.
*B41J 29/393* (2006.01)
*G01N 21/25* (2006.01)
*H04N 1/60* (2006.01)
*G01J 3/02* (2006.01)
*G01J 3/46* (2006.01)
*G01J 3/52* (2006.01)

(52) U.S. Cl.
CPC ............ *G01N 21/251* (2013.01); *G01J 3/0205* (2013.01); *G01J 3/462* (2013.01); *G01J 3/524* (2013.01); *H04N 1/6033* (2013.01)

(58) Field of Classification Search
None
See application file for complete search history.

(56) References Cited

U.S. PATENT DOCUMENTS

| | | | |
|---|---|---|---|
| 2009/0021738 A1* | 1/2009 | Horita | 356/404 |
| 2011/0075172 A1* | 3/2011 | Katayama | 358/1.9 |
| 2012/0069411 A1 | 3/2012 | Satoh et al. | |
| 2012/0236308 A1 | 9/2012 | Satoh | |
| 2013/0027720 A1* | 1/2013 | Satoh | 358/1.9 |
| 2013/0027721 A1 | 1/2013 | Kobayashi et al. | |
| 2013/0135484 A1 | 5/2013 | Satoh et al. | |
| 2013/0208289 A1 | 8/2013 | Satoh et al. | |
| 2013/0229671 A1 | 9/2013 | Yokozawa et al. | |
| 2013/0242319 A1 | 9/2013 | Suzuki et al. | |
| 2013/0242320 A1 | 9/2013 | Suzuki et al. | |

(Continued)

FOREIGN PATENT DOCUMENTS

| | | |
|---|---|---|
| JP | 2010-241061 | 10/2010 |
| JP | 2010241061 A * | 10/2010 |
| JP | 2013-051671 | 3/2013 |

*Primary Examiner* — Bradley Thies
(74) *Attorney, Agent, or Firm* — Duft Bornsen & Fettig LLP

(57) ABSTRACT

An image forming apparatus includes a printing unit that prints at least one object image using a color material; a color information acquiring unit that acquires color information of the object image; and a control unit that starts one of colorimetry of the object image using the color information acquired by the color information acquiring unit and color adjustment of the printing unit after a variation amount of color information of the object image measured at different points of time is equal to or smaller than a predetermined threshold.

3 Claims, 26 Drawing Sheets

(56) References Cited

U.S. PATENT DOCUMENTS

| | | |
|---|---|---|
| 2013/0242321 A1 | 9/2013 | Okada et al. |
| 2013/0242361 A1 | 9/2013 | Matsumoto et al. |
| 2013/0258368 A1 | 10/2013 | Shigemoto et al. |
| 2013/0258369 A1 | 10/2013 | Suzuki et al. |

* cited by examiner

FIG.7

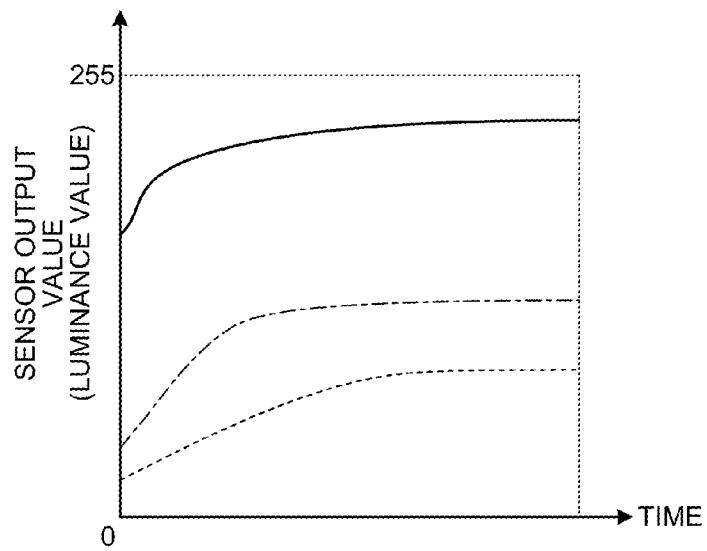

FIG.8

| FACTOR | INFLUENCE ON STABILIZING TIME |
|---|---|
| TYPE OF PRINTING MEDIUM | STABILIZATION BECOMES DIFFICULT AS INK PERMEABILITY OF PRINTING MEDIUM IS LOWERED |
| TEMPERATURE | STABILIZATION BECOMES DIFFICULT AS TEMPERATURE IS LOWERED |
| HUMIDITY | STABILIZATION BECOMES DIFFICULT AS HUMIDITY IS RAISED |
| USE AMOUNT OF INK | STABILIZATION BECOMES DIFFICULT AS INK AMOUNT PER UNIT AREA IS INCREASED |
| TYPE OF INK | STABILIZING TIME IS DIFFERENT DEPENDING ON CONTENTS |

| TIME | SENSOR OUTPUT VALUE (LUMINANCE VALUE) | | |
|---|---|---|---|
| | R | G | B |
| 0 | 70 | 50 | 135 |
| t0 | 100 | 75 | 160 |
| t1 | 120 | 90 | 175 |
| t2 | 130 | 109 | 183 |
| t3 | 132 | 115 | 190 |
| t4 | 134 | 120 | 193 |
| t5 | 135 | 120 | 195 |
| t6 | 135 | 120 | 195 |

VARIATION AMOUNT IS EQUAL TO OR SMALLER THAN THRESHOLD Th

| PATCH NUMBER | Rd | Gd | Bd | Ld | ad | bd | Xd | Yd | Zd |
|---|---|---|---|---|---|---|---|---|---|
| 1 | 3 | 8 | 5 | 6 | 7 | 2 | | | |
| 2 | | | | | | | | | |
| 3 | | | | | | | | | |
| ... | | | | | | | | | |
| ... | | | | | | | | | |
| | | | | | | | | | |
| ... | | | | | | | | | |
| 72 | | | | | | | | | |

INITIAL REFERENCE RGB VALUE (RdGdBd) spans Rd, Gd, Bd columns. Tb1

(a)

(b)

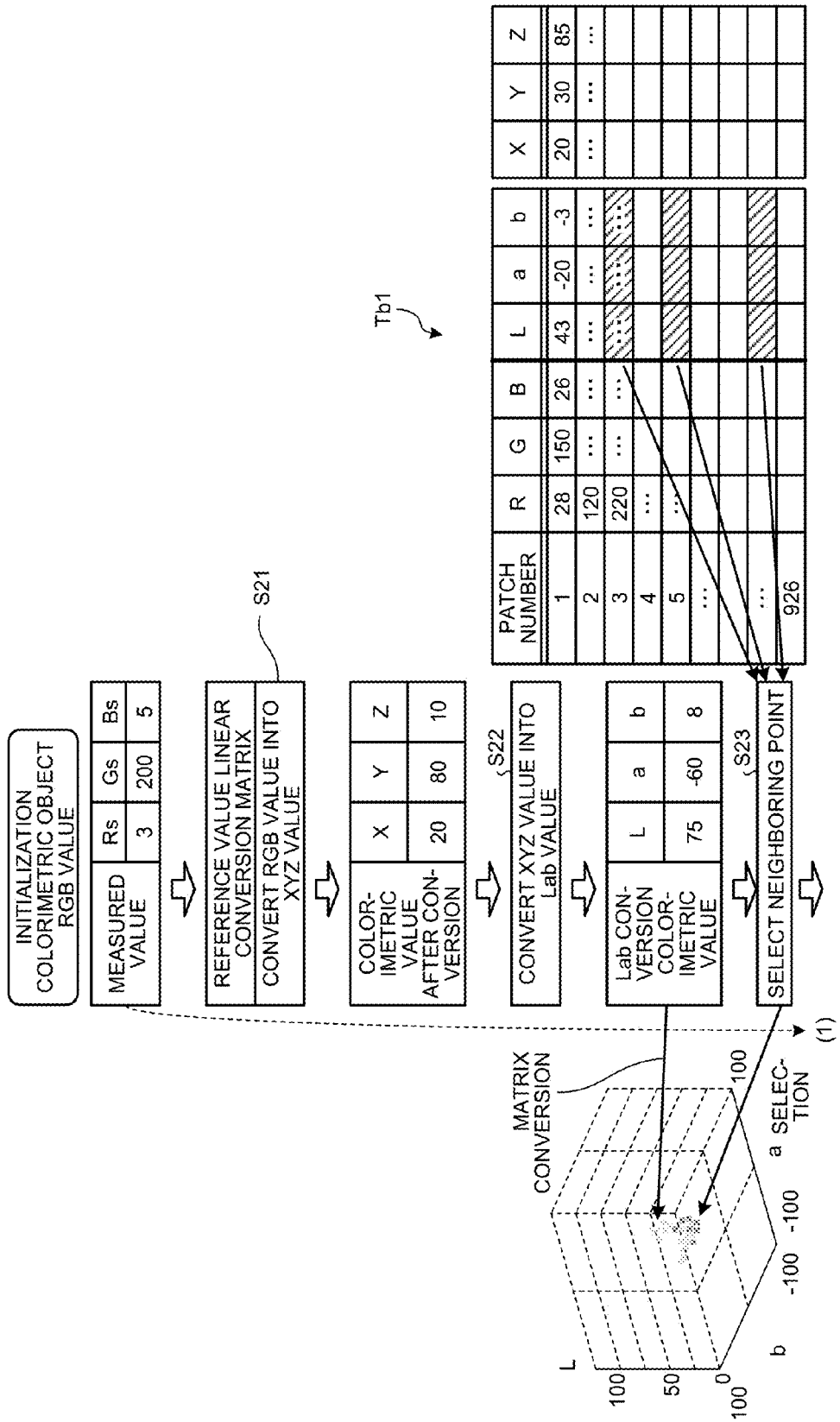

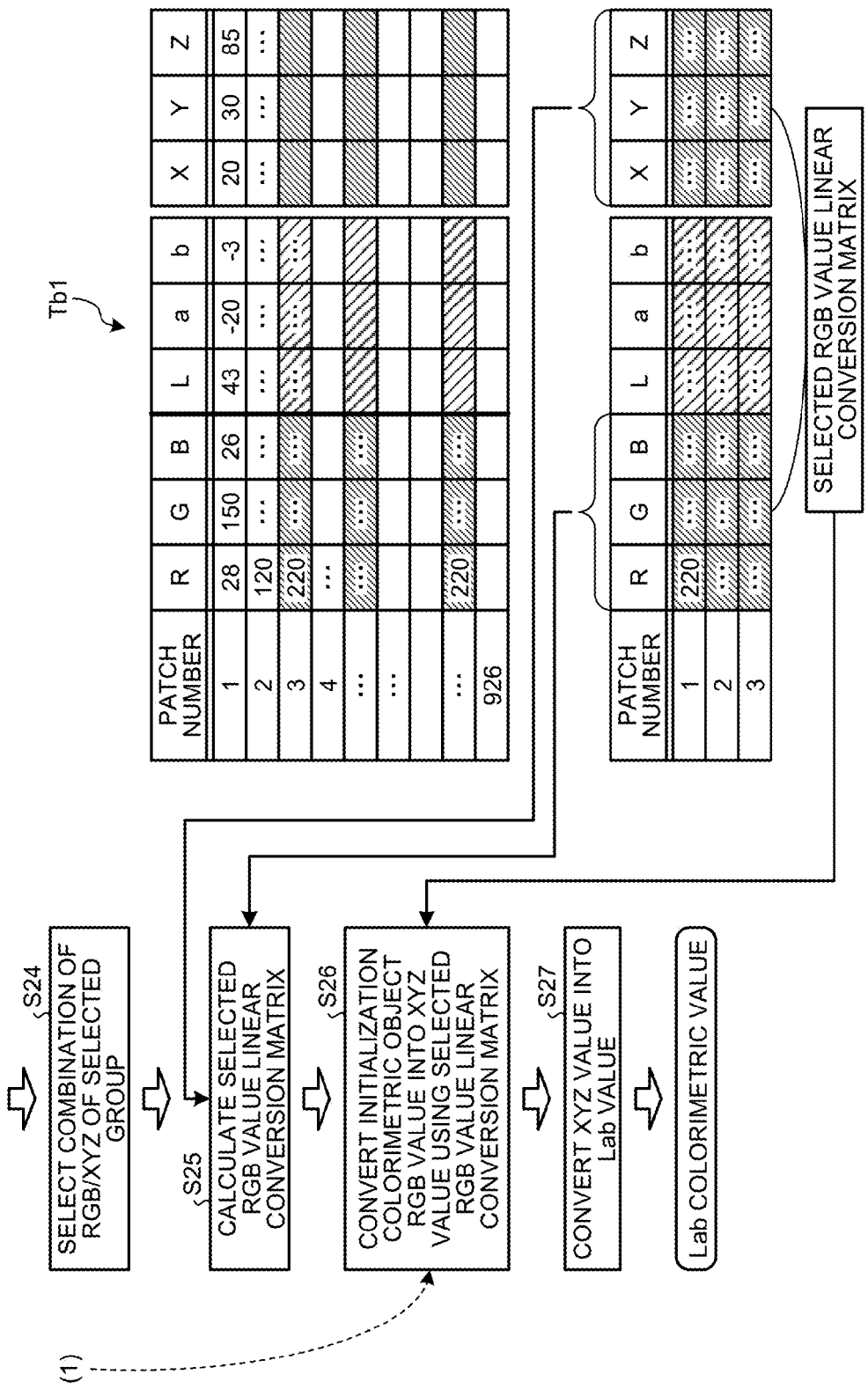

(a)

(b)

| TIME | RGB MEASURE-MENT RESULT (R+G+B) | |
|---|---|---|
| $T_P[8]$ | 610 | |
| T0 | 650 | |
| T1 | 675 | |
| T2 | 690 | |
| T3 | 700 | STABILIZING/START COLORIMETRY OF EIGHTH ROW |
| T4 | 700 | |
| T5 | 580 | |
| T6 | 595 | |
| T7 | 607 | |
| T8 | 612 | STABILIZING/START COLORIMETRY OF SEVENTH ROW |
| T9 | 612 | |

IMAGE FORMING APPARATUS, CALIBRATION METHOD, AND DRYING DETERMINATION METHOD

CROSS-REFERENCE TO RELATED APPLICATIONS

The present application claims priority to and incorporates by reference the entire contents of Japanese Patent Application No. 2013-254553 filed in Japan on Dec. 9, 2013 and Japanese Patent Application No. 2014-243562 filed in Japan on Dec. 1, 2014.

BACKGROUND OF THE INVENTION

1. Field of the Invention

The present invention relates to an image forming apparatus, a calibration method, and a drying determination method.

2. Description of the Related Art

In the related art, as a calibration method in an image forming apparatus, known is a technique of performing colorimetry, with a colorimeter, on a pattern printed by the image forming apparatus using a color material, and updating a correction value for performing gradation correction of density based on an obtained colorimetric value (for example, refer to Japanese Patent Application Laid-open No. 2010-241061). The color of the pattern printed by the image forming apparatus using a color material is not stabilized until the color material of the pattern is dried. Accordingly, in the technique disclosed in Japanese Patent Application Laid-open No. 2010-241061, drying standby time is set corresponding to print conditions such as a temperature and humidity in pattern printing, a type of a printing medium, and a printing resolution, and colorimetry for the pattern is started to perform appropriate calibration when the drying standby time has elapsed after printing the pattern.

However, there are many combinations of the temperature and the humidity at the time of printing, the type of the printing medium, and the printing resolution. For example, as the type of the printing medium, there are a large number of types of glossy paper. Due to this, in the technique disclosed in Japanese Patent Application Laid-open No. 2010-241061, it is difficult to correctly set the drying standby time, and unnecessary drying standby time may be generated.

SUMMARY OF THE INVENTION

It is an object of the present invention to at least partially solve the problems in the conventional technology.

According to an embodiment, there is provided an image forming apparatus that includes a printing unit that prints at least one object image using a color material; a color information acquiring unit that acquires color information of the object image; and a control unit that starts one of colorimetry of the object image using the color information acquired by the color information acquiring unit and color adjustment of the printing unit after a variation amount of color information of the object image measured at different points of time is equal to or smaller than a predetermined threshold.

According to another embodiment, there is provided a calibration method executed in an image forming apparatus. The calibration method includes printing at least one object image using a color material; measuring color information of the object image at different points of time; determining whether a variation amount of the color information is equal to or smaller than a predetermined threshold; and acquiring color information of the object image and then starting one of colorimetry using the color information and color adjustment of the image forming apparatus after the variation amount is equal to or smaller than the threshold.

According to still another embodiment, there is provided a drying determination method for determining drying of an image printed using a color material. The drying determination method includes acquiring color information of a part of the image; and determining that the image is dried when a variation amount of the color information measured at different points of time is equal to or smaller than a predetermined threshold.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a diagram illustrating a temporal change in an RGB value measured by capturing an image of an arbitrary patch with the colorimetric camera;

FIG. 8 is a diagram listing factors that affect stabilizing time in a table;

FIG. 19 is a diagram for explaining basic colorimetric processing;

FIG. 20 is a diagram for explaining the basic colorimetric processing;

DETAILED DESCRIPTION OF THE PREFERRED EMBODIMENTS

The following describes embodiments of an image forming apparatus, a calibration method and a drying determination method according to the present invention in detail with reference to the attached drawings. In the following embodiments, a serial-head ink-jet printer is exemplified as an example of the image forming apparatus to which the present invention is applied.

Mechanical Configuration of Image Forming Apparatus

Figure 1:
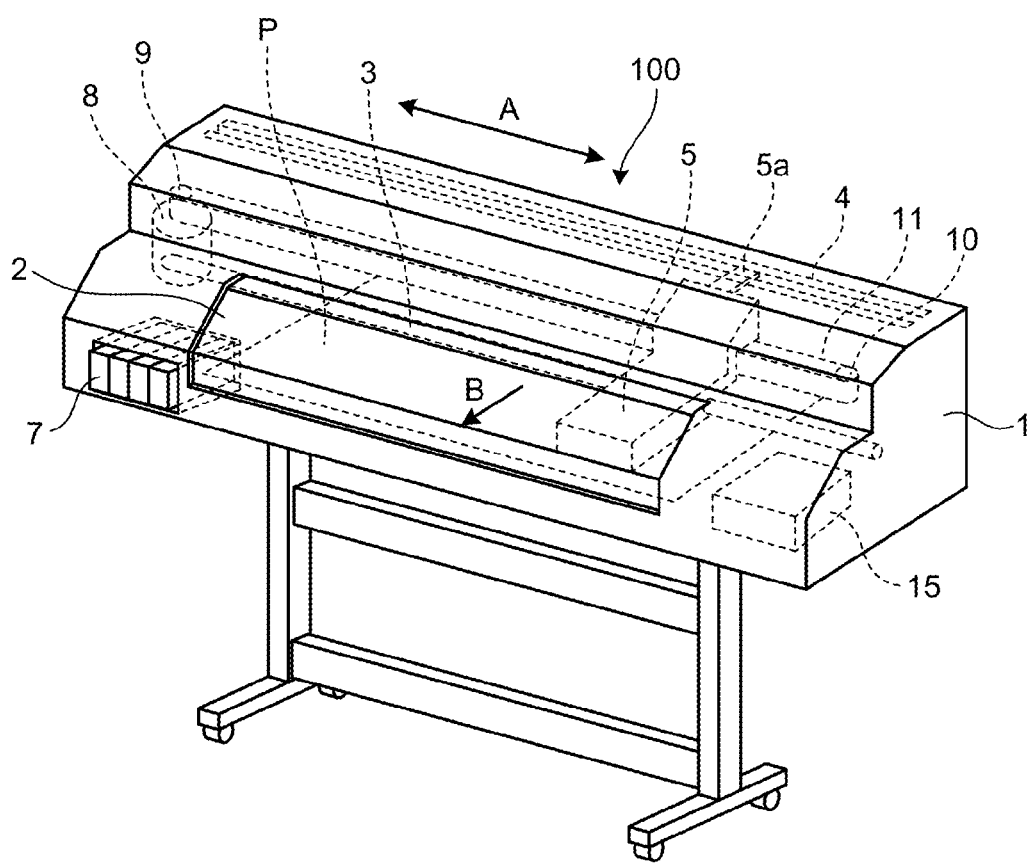
FIG. 1 is a perspective view seeing through the inside of an image forming apparatus.
Figure 2:
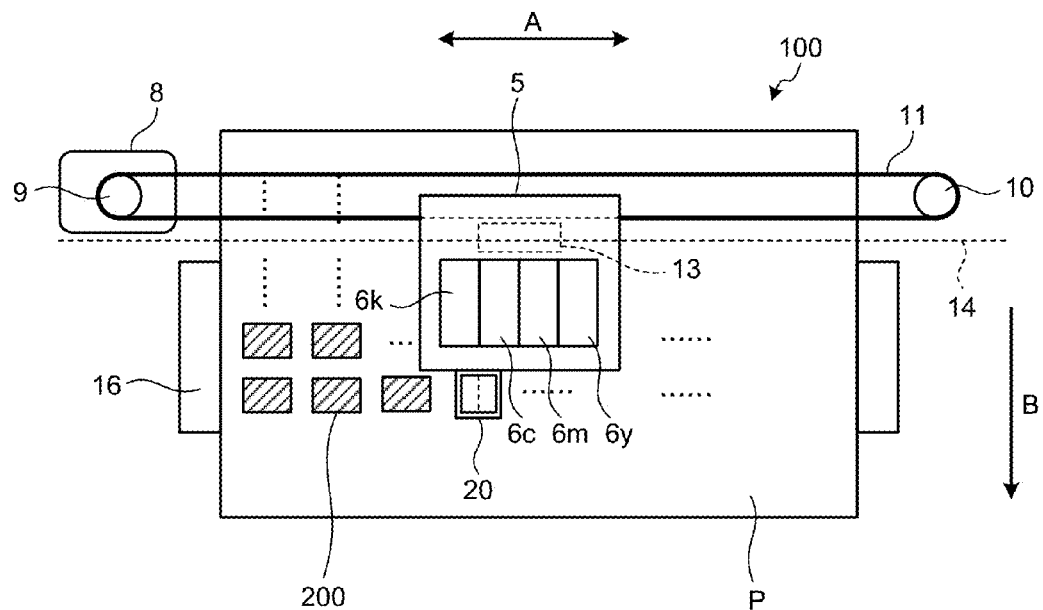
FIG. 2 is a top view illustrating a mechanical configuration of the inside of the image forming apparatus.
Figure 3:
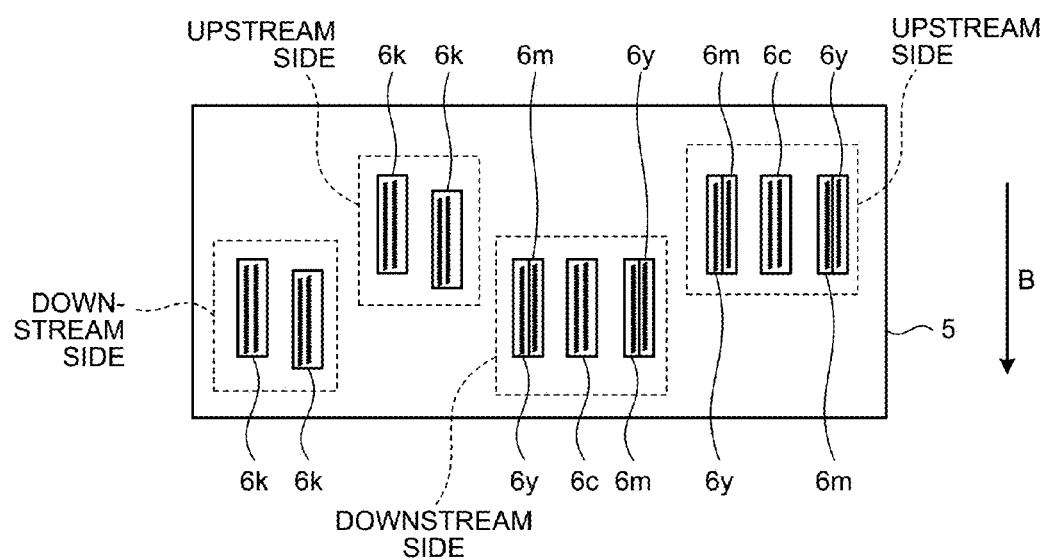
FIG. 3 is a diagram for explaining an arrangement example of a recording head mounted on a carriage.

First, the following describes a mechanical configuration of an image forming apparatus 100 according to the embodiment with reference to FIGS. 1 to 3. FIG. 1 is a perspective view seeing through the inside of the image forming apparatus 100. FIG. 2 is a top view illustrating the mechanical configuration of the inside of the image forming apparatus 100. FIG. 3 is a diagram for explaining an arrangement example of a recording head 6 mounted on a carriage 5.

As illustrated in FIG. 1, the image forming apparatus 100 according to the embodiment includes the carriage (base material) 5 that reciprocates in a main-scanning direction (arrow A direction in the drawing). The carriage 5 is supported by a main guide rod 3 extended along the main-scanning direction. A connecting piece 5a is arranged on the carriage 5. The connecting piece 5a is engaged with a sub-guide member 4 arranged in parallel with the main guide rod 3, and stabilizes a posture of the carriage 5.

As illustrated in FIG. 2, four recording heads 6y, 6m, 6c, and 6k are mounted on the carriage 5. The recording head 6y is a recording head that ejects yellow (Y) ink. The recording head 6m is a recording head that ejects magenta (M) ink. The recording head 6c is a recording head that ejects cyan (C) ink. The recording head 6k includes a plurality of recording heads that eject black (Bk) ink. Hereinafter, these recording heads 6y, 6m, 6c, and 6k may be collectively referred to as a recording head 6 in some cases. The recording head 6 is supported by the carriage 5 such that the ejection face (nozzle face) of the recording head 6 faces downward (printing medium P side).

A cartridge 7 serving as an ink supplier for supplying ink to the recording head 6 is not mounted on the carriage 5, and is arranged at a predetermined position in the image forming apparatus 100. The cartridge 7 is coupled to the recording head 6 via a pipe (not illustrated). The ink is supplied from the cartridge 7 to the recording head 6 through the pipe. The ink is a color material used by the image forming apparatus 100 to form an image on the printing medium P.

The carriage 5 is coupled to a timing belt 11 stretched between a driving pulley 9 and a driven pulley 10. The driving pulley 9 is rotated by being driven by a main scanning motor 8. The driven pulley 10 has a mechanism that adjusts a distance between the driven pulley 10 and the driving pulley 9, and plays a role that gives predetermined tension to the timing belt 11. The carriage 5 reciprocates in the main-scanning direction when the timing belt 11 is driven and advanced by the main scanning motor 8. For example, as illustrated in FIG. 2, movement of the carriage 5 in the main-scanning direction is controlled based on an encoder value obtained by detecting a mark on an encoder sheet 14 with an encoder sensor 13 provided on the carriage 5.

The image forming apparatus 100 according to the embodiment includes a maintenance mechanism 15 for maintaining reliability of the recording head 6. The maintenance mechanism 15 performs cleaning or capping of the ejection face of the recording head 6, and discharges unnecessary ink from the recording head 6.

As illustrated in FIG. 2, a platen 16 is arranged at a position opposite to the ejection face of the recording head 6. The platen 16 is used for supporting the printing medium P when the ink is ejected from the recording head 6 to the printing medium P. The image forming apparatus 100 according to the embodiment is a wide machine in which a moving distance of the carriage 5 in the main-scanning direction is long. Due to this, the platen 16 is configured by connecting a plurality of plate members in the main-scanning direction (moving direction of the carriage 5). The printing medium P is sandwiched by conveyance rollers driving by a sub-scanning motor (not illustrated), and is intermittently conveyed on the platen 16 in the sub-scanning direction.

The recording head 6 includes a plurality of nozzle arrays, and ejects the ink from the nozzle arrays to the printing medium P conveyed on the platen 16 to print an image on the printing medium P. In the embodiment, to secure a large width of an image that can be printed in one scanning process by the carriage 5, the carriage 5 includes the recording head 6 on the upstream side and the recording head 6 on the downstream side mounted thereon as illustrated in FIG. 3. The number of recording heads 6k that are mounted on the carriage 5 to eject the black ink is twice the number of the recording heads 6y, 6m, and 6c that eject color ink. The recording heads 6y and 6m are separately arranged on the left and the right. This is because the order of color overlapping should be kept in a reciprocating operation of the carriage 5, and the color should be prevented from changing between an outward route and a return route. The arrangement of the recording head 6 illustrated in FIG. 3 is merely an example and not limited to the arrangement illustrated in FIG. 3.

The above-described components included in the image forming apparatus 100 according to the embodiment are arranged inside an exterior body 1. A cover member 2 is arranged on the exterior body 1 in an openable manner. When maintenance of the image forming apparatus 100 is performed or paper jam occurs, each of the components arranged inside the exterior body 1 can be treated by opening the cover member 2.

The image forming apparatus 100 according to the embodiment intermittently conveys the printing medium P in the sub-scanning direction (arrow B direction in the drawing).

While the conveyance of the printing medium P in the sub-scanning direction is stopped, the image forming apparatus 100 causes the carriage 5 to be moved in the main-scanning direction and ejects the ink from the nozzle arrays of the recording head 6 mounted on the carriage 5 to the printing medium P on the platen 16 to print an image on the printing medium P.

Specifically, to perform calibration, such as color adjustment, of the image forming apparatus 100, the ink is ejected from the nozzle arrays of the recording head 6 mounted on the carriage 5 to the printing medium P on the platen 16 to print a test pattern including a large number of patches 200 arranged therein (printing unit). Colorimetry is then performed on each of the patches 200 included in the test pattern. Each patch 200 included in the test pattern is an image obtained by printing a pattern of standard color actually using the ink by the image forming apparatus 100, and reflects characteristics specific to the image forming apparatus 100. Accordingly, it is possible to generate or correct a device profile describing the characteristics specific to the image forming apparatus 100 using a colorimetric value of each patch 200. The image forming apparatus 100 can output an image with high reproducibility by performing color conversion between a standard color space and a device-dependent color based on the device profile.

The image forming apparatus 100 according to the embodiment includes a colorimetric camera (color information acquiring unit) 20 for performing colorimetry on each of the patches 200 included in the test pattern printed on the printing medium P. As illustrated in FIG. 2, the colorimetric camera 20 is supported by the carriage 5 on which the recording head 6 is mounted. The colorimetric camera 20 moves above the printing medium P due to the conveyance of the printing medium P on which the test pattern is printed and the movement of the carriage 5, and captures an image when reaching a position opposite to each patch 200. The colorimetric camera 20 then calculates the colorimetric value of the patch 200 based on an RGB value (color information) of the image obtained by the image capturing. In the embodiment, an example will be described in which color adjustment of the image forming apparatus 100 is performed by using the colorimetric value of the patch 200 calculated from the RGB value of the patch 200 obtained by the image capturing; however, the color adjustment of the image forming apparatus 100 may be performed by using the RGB value of the patch 200 obtained by the image capturing. In this case, the amount of ink ejected to the printing medium P is adjusted by the color adjustment.

Specific Example of Colorimetric Camera

Figure 4A:
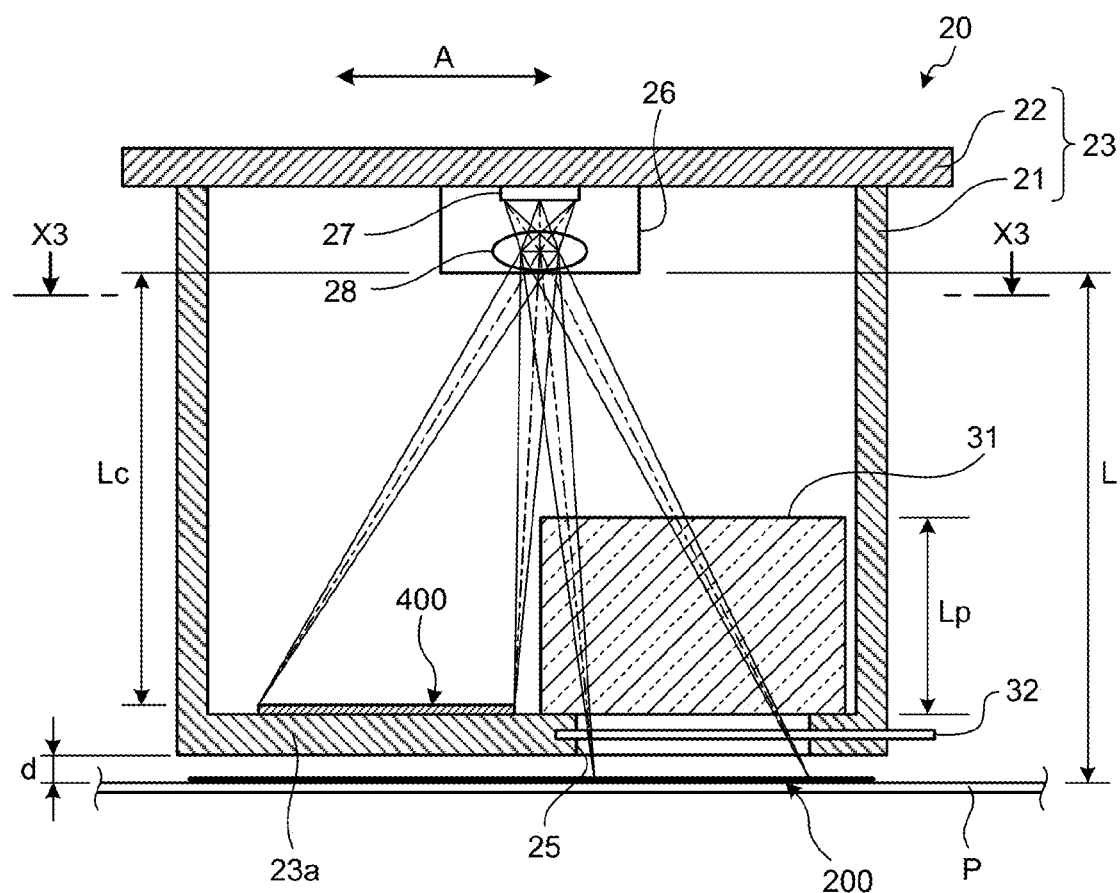
FIG. 4A is a vertical cross-sectional view (cross-sectional view along the line X1-X1 in FIG. 4C) of a colorimetric camera.
Figure 4B:
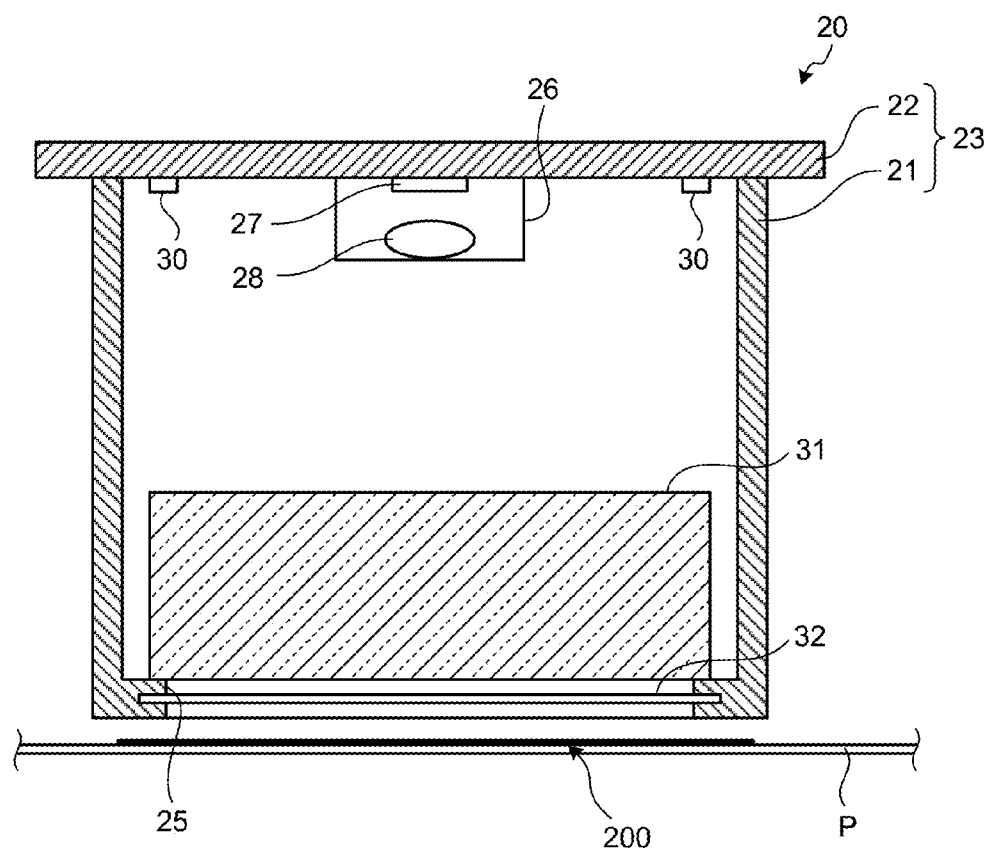
FIG. 4B is another vertical cross-sectional view (cross-sectional view along the line X2-X2 in FIG. 4C) of the colorimetric camera.
Figure 4C:
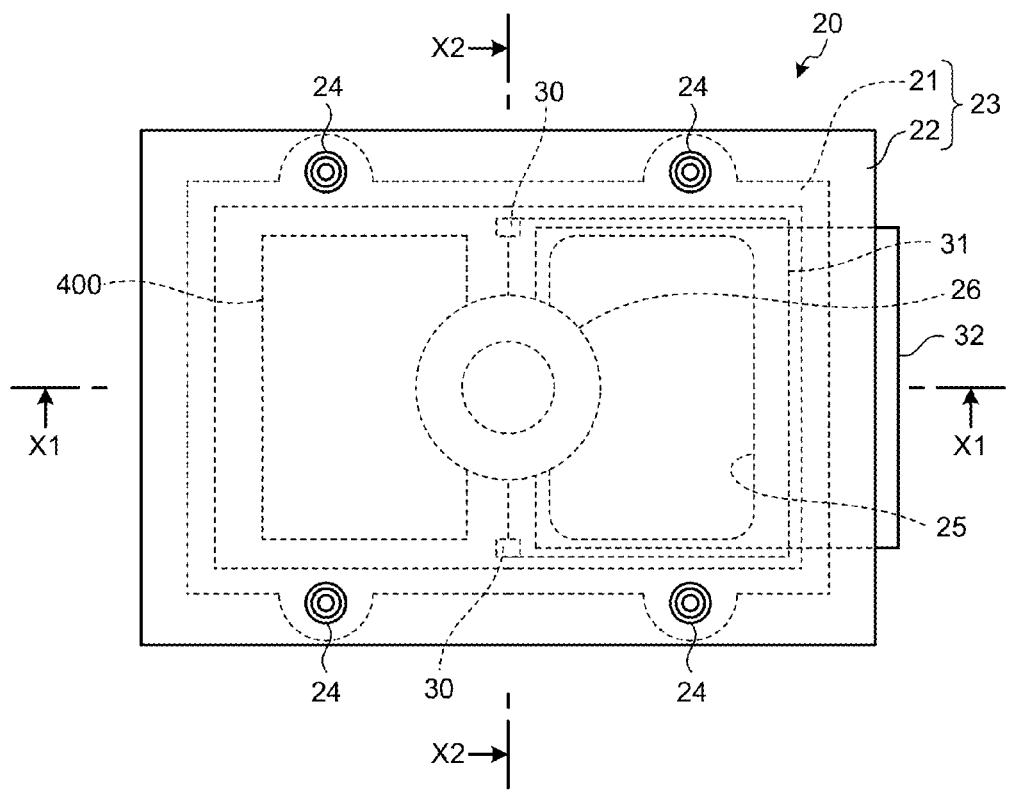
FIG. 4C is a top view seeing through the inside of the colorimetric camera.
Figure 4D:
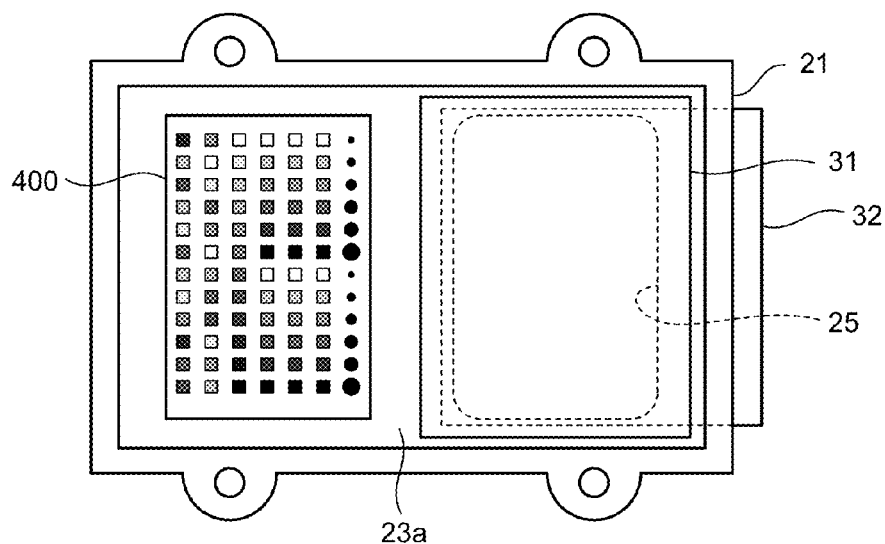
FIG. 4D is a plan view of a bottom face part of a housing viewed from the X3 direction in FIG. 4A.

Next, the following describes a specific example of the colorimetric camera 20 in detail with reference to FIGS. 4A to 4D. FIGS. 4A to 4D are diagrams illustrating an example of a mechanical configuration of the colorimetric camera 20. FIG. 4A is a vertical cross-sectional view (cross-sectional view along the line X1-X1 in FIG. 4C) of the colorimetric camera 20. FIG. 4B is another vertical cross-sectional view (cross-sectional view along the line X2-X2 in FIG. 4C) of the colorimetric camera 20. FIG. 4C is a top view seeing through the inside of the colorimetric camera 20. FIG. 4D is a plan view of a bottom face part of a housing viewed from the X3 direction in FIG. 4A.

The colorimetric camera 20 includes a housing 23 configured by combining a frame body 21 and a substrate 22. The frame body 21 is formed into a bottomed cylindrical shape one end of which being an upper surface of the housing 23 is opened. The substrate 22 is fastened to the frame body 21 with a fastening member 24 so as to close an open end of the frame body 21 and configure the upper surface of the housing 23, and integrated with the frame body 21.

The housing 23 is fixed to the carriage 5 so that a bottom face part 23a thereof is opposite to the printing medium P on the platen 16 with a predetermined gap d. An opening 25 is arranged on the bottom face part 23a of the housing 23 opposite to the printing medium P for enabling the patch 200 (colorimetric object) included in the test pattern formed on the printing medium P to be photographed from the inside of the housing 23.

A sensor unit 26 that captures an image is arranged inside the housing 23. The sensor unit 26 includes a two-dimensional image sensor 27 such as a charge-coupled device (CCD) sensor or a complementary metal oxide semiconductor (CMOS) sensor, and an imaging forming lens 28 that forms an optical image in an imaging target region of the sensor unit 26 on a sensor face of the two-dimensional image sensor 27. The two-dimensional image sensor 27 is mounted, for example, on an inner face of the substrate 22 (component mounting face) so that the sensor face faces the bottom face part 23a of the housing 23. The imaging forming lens 28 is fixed to the two-dimensional image sensor 27 in a positioned state so as to keep a positional relation that is determined corresponding to an optical characteristic thereof.

A reference chart 400 is arranged on the inner face of the bottom face part 23a of the housing 23 that is opposite to the sensor unit 26 so as to be adjacent to the opening 25 arranged on the bottom face part 23a. The reference chart 400 is captured by the sensor unit 26 together with the patch 200 to perform colorimetry on the patch 200 included in the test pattern. The reference chart 400 is arranged on the bottom face part 23a of the housing 23 so as to be included in the capturing target region of the sensor unit 26 in capturing an image of the patch 200 as the colorimetric object arranged outside the housing 23. Details about the reference chart 400 will be described later.

An illumination light source 30 that illuminates the capturing target region of the sensor unit 26 is arranged inside the housing 23. For example, a light emitting diode (LED) is used as the illumination light source 30. In the embodiment, two LEDs are used as the illumination light source 30. These two LEDs used as the illumination light source 30 are mounted on the inner face of the substrate 22 together with the two-dimensional image sensor 27 of the sensor unit 26. It is sufficient that the illumination light source 30 is arranged at a position where the capturing target region of the sensor unit 26 can be uniformly illuminated. The illumination light source 30 is not necessarily mounted on the substrate 22 in a direct manner. In the embodiment, the LED is used as the illumination light source 30. However, a type of the light source is not limited to the LED. For example, organic EL and the like may be used as the illumination light source 30. When the organic EL is used as the illumination light source 30, illumination light that is close to spectral distribution of sunlight can be obtained, so that improvement in colorimetric accuracy can be expected.

In the embodiment, as illustrated in FIG. 4C, these two LEDs are arranged so that a projection position on the bottom face part 23a is in a region between the opening 25 and the reference chart 400 and is symmetrical with respect to the sensor unit 26 when vertically looking down the two LEDs used as the illumination light source 30 from the substrate 22 side toward the bottom face part 23a side of the housing 23. In other words, a line connecting the two LEDs used as the illumination light source 30 passes through the center of the imaging forming lens 28 of the sensor unit 26, and the opening 25 and the reference chart 400 are arranged at a position that is line symmetric with respect to the line connecting the two LEDs. By arranging two LEDs used as the illumination light source 30 in this manner, it is possible to illuminate the patch 200 as the colorimetric object outside the housing 23 and the reference chart 400 inside the housing 23 under substantially the same condition.

To illuminate the patch 200 outside the housing 23 under the illumination condition same as that of the reference chart 400 arranged inside the housing 23, the patch 200 should be illuminated only with illumination light from the illumination light source 30 while preventing the patch 200 from being exposed to external light. To prevent the patch 200 from being exposed to the external light, it is effective to reduce the gap d between the bottom face part 23a of the housing 23 and the printing medium P, and to cause the external light toward the patch 200 to be blocked by the housing 23. However, when the gap d between the bottom face part 23a of the housing 23 and the printing medium P is excessively reduced, the printing medium P may be brought into contact with the bottom face part 23a of the housing 23, so that the image cannot be appropriately captured in some cases. Accordingly, the gap d between the bottom face part 23a of the housing 23 and the printing medium P is preferably set to be a small value in a range in which the printing medium P is not in contact with the bottom face part 23a of the housing 23 considering planarity of the printing medium P. For example, when the gap d between the bottom face part 23a of the housing 23 and the printing medium P is set to about 1 mm to 2 mm, the printing medium P is prevented from being in contact with the bottom face part 23a of the housing 23, and the patch 200 formed on the printing medium P can be effectively prevented from being exposed to the external light.

An optical path length changing member 31 is arranged inside the housing 23 so as to block the opening 25 from the inner face side. The optical path length changing member 31 is an optical element of refractive index n (n is an arbitrary number) having sufficient transmittance with respect to light from the illumination light source 30 (illumination light). The optical path length changing member 31 is arranged in an optical path between the patch 200 outside the housing 23 and the sensor unit 26, and has a function for bringing an image forming surface of an optical image of the patch 200 close to an image forming surface of an optical image of the reference chart 400. That is, in the colorimetric camera 20 according to the embodiment, the optical path length changing member 31 is arranged in the optical path between the patch 200 and the sensor unit 26 to cause the image forming surface of the optical image of the patch 200 outside the housing 23 and the image forming surface of the reference chart 400 inside the housing 23 to be aligned with the sensor face of the two-dimensional image sensor 27 of the sensor unit 26.

When the light passes through the optical path length changing member 31, an optical path length is extended corresponding to the refractive index n of the optical path length changing member 31, and the image appears to be lifted. A lifting amount C of the image can be obtained from the following expression assuming that the length of the optical path length changing member 31 in an optical axis direction is Lp.

$$C = Lp(1 - 1/n)$$

Assuming that a distance between the principal point of the imaging forming lens 28 of the sensor unit 26 and the reference chart 400 is Lc, a distance L between the principal point of the imaging forming lens 28 and a front-side focal plane (imaging surface) of the optical image transmitted through the optical path length changing member 31 can be obtained from the following expression.

$$L = Lc + Lp(1 - 1/n)$$

When the refractive index n of the optical path length changing member 31 is set to 1.5, L=Lc+Lp(1/3) is satisfied, so that the optical path length of the optical image transmitted through the optical path length changing member 31 can be increased by about ⅓ of the length Lp of the optical path length changing member 31 in the optical axis direction. In this case, for example, when Lp=9 [mm], L=Lc+3 [mm] is satisfied. Accordingly, when imaging is performed in a state in which a difference between the distance from the sensor unit 26 to the reference chart 400 and the distance from the sensor unit 26 to the patch 200 is 3 mm, a rear-side focal plane (image forming surface) of the optical image of the reference chart 400 and a rear-side focal plane (image forming surface) of the optical image of the patch 200 can be both aligned with the sensor face of the two-dimensional image sensor 27 of the sensor unit 26.

As described above, the image forming apparatus 100 according to the embodiment is configured to eject the ink from the nozzle arrays of the recording head 6 mounted on the carriage 5 to the printing medium P on the platen 16 to print the image on the printing medium P. Due to this, when the ink is ejected from the nozzle arrays of the recording head 6, mist-like fine ink particles (hereinafter, such fine ink particles are referred to as "mist") are generated. If the mist generated in printing enters the housing 23 via the opening 25 from the outside of the housing 23 of the colorimetric camera 20 that is fixed to the carriage 5, the mist that enters the housing 23 may adhere to the sensor unit 26, the illumination light source 30, or the optical path length changing member 31, so that a correct RGB value cannot be obtained in performing colorimetry on the patch 200 in some cases. Accordingly, in the colorimetric camera 20 according to the embodiment, an anti-mist glass plate 32 is arranged at the opening 25 provided to the bottom face part 23a of the housing 23 to prevent the mist generated in printing from entering the housing 23.

The anti-mist glass plate 32 is a transparent optical element having sufficient transmittance with respect to the light from the illumination light source 30 (illumination light), and is formed into a plate shape having a size that can cover the entire opening 25. The anti-mist glass plate 32 is mounted to a slit formed along the bottom face part 23a of the housing 23, and closes the entire opening 25 provided to the bottom face part 23a of the housing 23. The slit to which the anti-mist glass plate 32 is mounted is opened at the side surface of the housing 23. The anti-mist glass plate 32 can be inserted from the side surface of the housing 23 to be mounted to the slit. The anti-mist glass plate 32 can be removed through the side surface of the housing 23 and appropriately replaced.

Specific Example of Reference Chart

Figure 5:
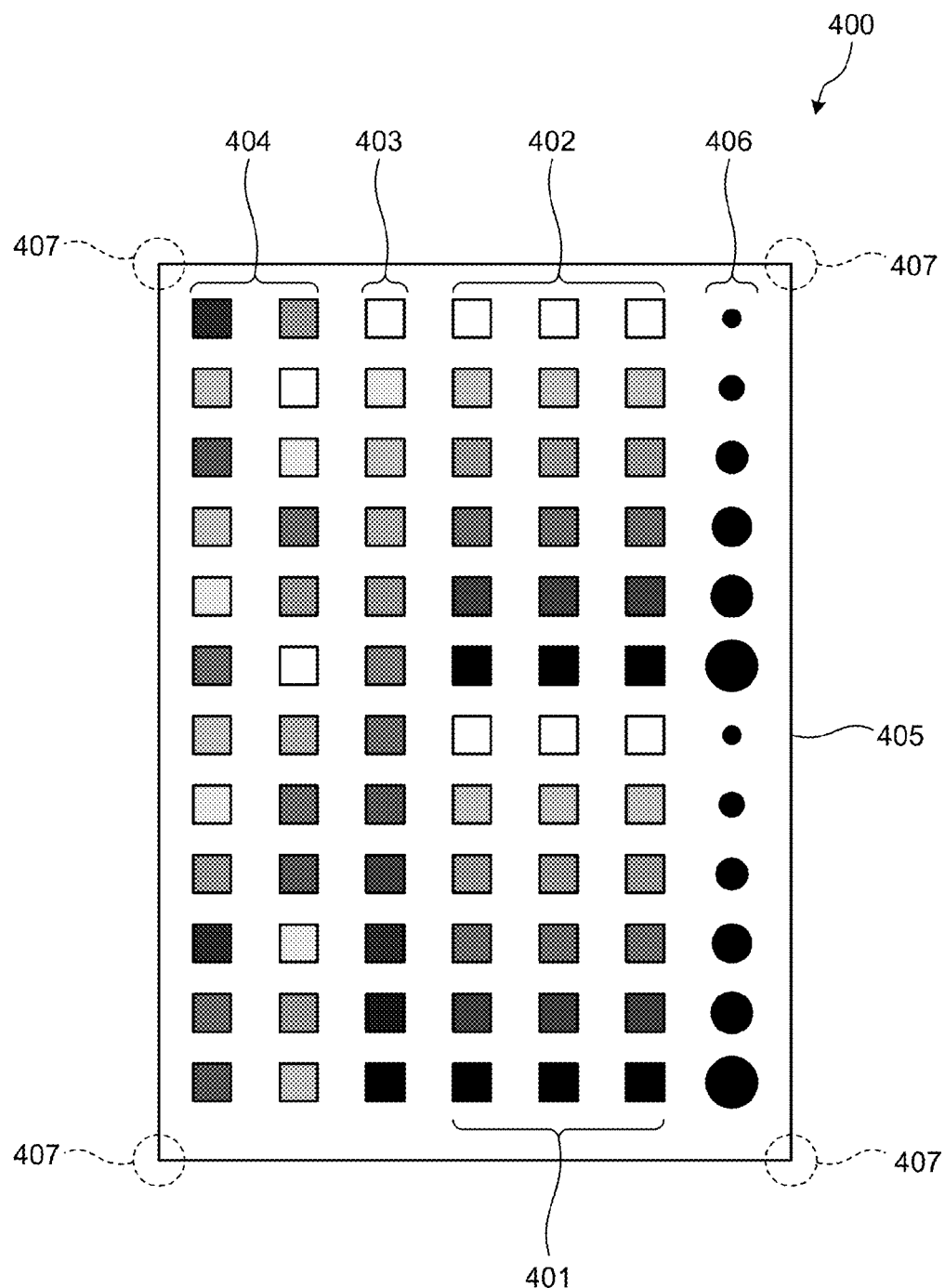
FIG. 5 is a diagram illustrating a specific example of a reference chart.

Next, the following describes the reference chart 400 arranged inside the housing 23 of the colorimetric camera 20 in detail with reference to FIG. 5. FIG. 5 is a diagram illustrating a specific example of the reference chart 400.

The reference chart 400 illustrated in FIG. 5 includes a plurality of reference patch arrays 401 to 404 in which reference patches for colorimetry are arrayed, a pattern array 406 for measuring a dot diameter, a line 405 for measuring a distance, and markers 407 for specifying a chart position.

The reference patch arrays 401 to 404 include the reference patch array 401 in which reference patches of primary colors of YMCK are arrayed in the order of gradation, the reference patch array 402 in which reference patches of secondary colors of RGB are arrayed in the order of gradation, the reference patch array (achromatic gradation pattern) 403 in which reference patches of a gray scale are arrayed in the order of gradation, and the reference patch array 404 in which reference patches of tertiary colors are arrayed. The pattern array 406 for measuring a dot diameter is a pattern array for measuring a geometric shape in which circular patterns having different sizes are arrayed in the order of size, and can be used for measuring a dot diameter of an image printed on the printing medium P.

The line 405 for measuring a distance is formed as a rectangular frame surrounding the reference patch arrays 401 to 404 and the pattern array 406 for measuring a dot diameter. The markers 407 for specifying a chart position are arranged at four corners of the line 405 for measuring a distance, and function as markers for specifying a position of each of the reference patches. By specifying the line 405 for measuring a distance and the markers 407 for specifying a chart position at the four corners thereof from the image of the reference chart 400 captured by the sensor unit 26, it is possible to specify the position of the reference chart 400 and the position of each reference patch or pattern.

Each reference patch included in the reference patch arrays 401 to 404 for colorimetry is used as a reference of a color tone reflecting an imaging condition of the colorimetric camera 20. The configuration of the reference patch arrays 401 to 404 for colorimetry arranged in the reference chart 400 is not limited to the example illustrated in FIG. 5, and an arbitrary reference patch array can be applied. For example, the reference patch a color range of which can be specified as widely as possible can be used. Alternatively, the reference patch array 401 of the primary colors of YMCK or the reference patch array 403 of a gray scale may include a patch of a colorimetric value of the ink used in the image forming apparatus 100. The reference patch array 402 of the secondary colors of RGB may include a patch of a colorimetric value that can be colored with the ink used in the image forming apparatus 100, and may use a standard color chart such as Japan Color colorimetric values of which are determined.

In the embodiment, used is the reference chart 400 that includes the reference patch arrays 401 to 404 having a typical patch (color chart) shape. However, the reference chart 400 does not necessarily have such a configuration including the reference patch arrays 401 to 404. The reference chart 400 may have a configuration in which a plurality of colors that can be used for colorimetry are arranged so as to be able to specify each position.

The reference chart 400 is arranged on the bottom face part 23a of the housing 23 of the colorimetric camera 20 to be adjacent to the opening 25, so that the sensor unit 26 can image the reference chart 400 and the patch 200 as the colorimetric object at the same time. In this case, "image the reference chart 400 and the patch 200 as the colorimetric object at the same time" means acquiring one-frame image data including the patch 200 as the colorimetric object and the reference chart 400. That is, even if there is a time difference between data acquisition processes for each pixel, the patch 200 and the reference chart 400 are assumed to be captured at the same time when the image data including the patch 200 and the reference chart 400 in one frame is acquired.

The mechanical configuration of the colorimetric camera 20 described above is merely an example, and various modifications and changes can be made. The image forming apparatus 100 according to the embodiment may include a colorimeter that can perform colorimetry on the patch 200 included in the test pattern, not limited to the colorimetric camera 20 described above. The image forming apparatus 100 may have a configuration including various types of colorimeters instead of the colorimetric camera 20.

Schematic Configuration of Control Mechanism of Image Forming Apparatus

Figure 6:
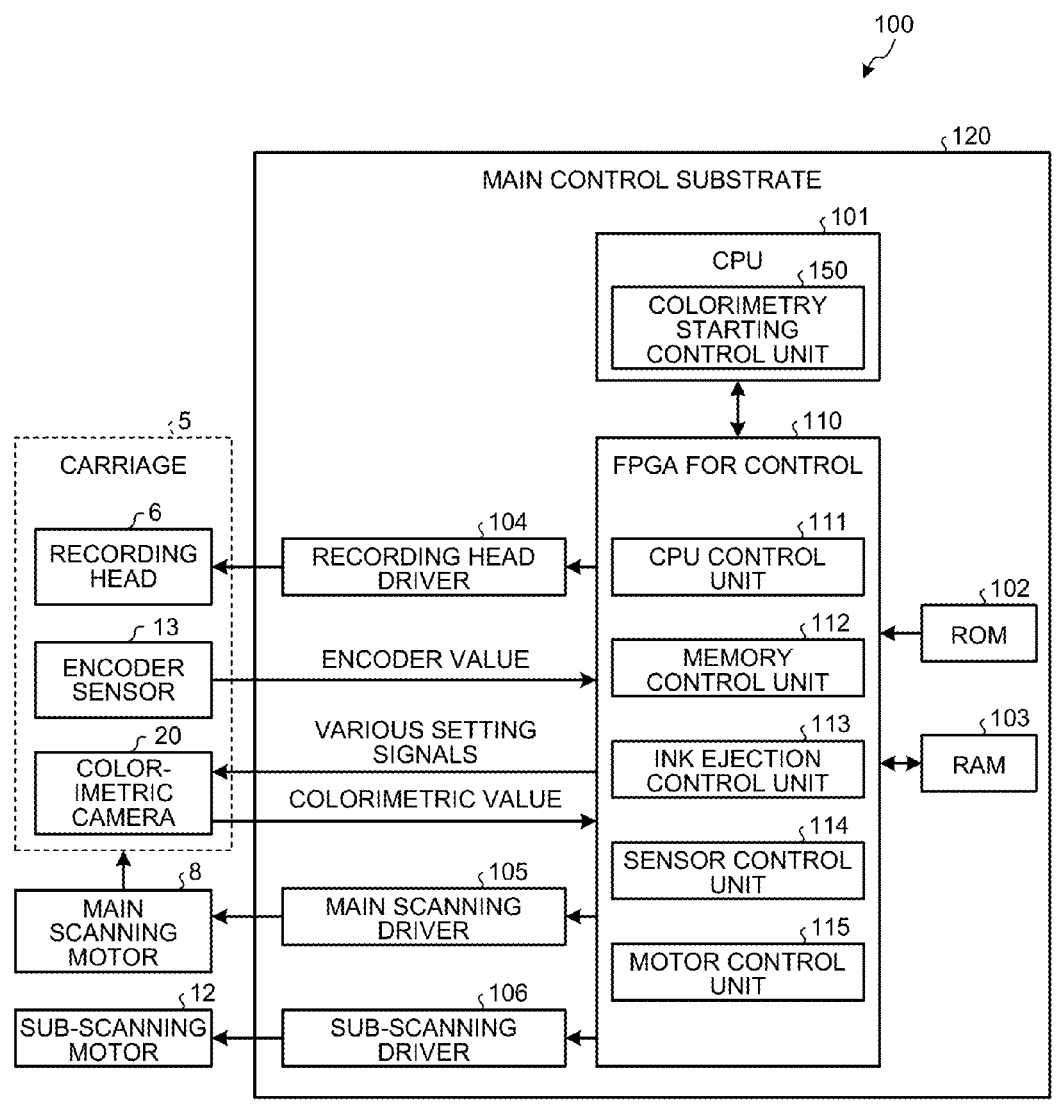
FIG. 6 is a control block diagram of the image forming apparatus.

Next, the following describes a schematic configuration of a control mechanism of the image forming apparatus 100 according to the embodiment with reference to FIG. 6. FIG. 6 is a block diagram illustrating the schematic configuration of the control mechanism of the image forming apparatus 100.

As illustrated in FIG. 6, the image forming apparatus 100 according to the embodiment includes a central processing unit (CPU) 101, a read only memory (ROM) 102, a random access memory (RAM) 103, a recording head driver 104, a main scanning driver 105, a sub-scanning driver 106, a field-programmable gate array (FPGA) 110 for control, the recording head 6, the colorimetric camera 20, the encoder sensor 13, the main scanning motor 8, and a sub-scanning motor 12. The CPU 101, the ROM 102, the RAM 103, the recording head driver 104, the main scanning driver 105, the sub-scanning driver 106, and the FPGA 110 for control are mounted on a main control substrate 120. The recording head 6, the encoder sensor 13, and the colorimetric camera 20 are mounted on the carriage 5 as described above.

The CPU 101 controls the entire image forming apparatus 100. For example, the CPU 101 utilizes the RAM 103 as a working area to execute various control programs stored in the ROM 102, and output a control command for controlling various operations in the image forming apparatus 100. Specifically, in the image forming apparatus 100 according to the embodiment, the CPU 101 implements a function as a colorimetry starting control unit 150 that optimizes the timing for starting colorimetry of each patch 200 included in the test pattern. Specific content of processing performed by the colorimetry starting control unit 150 will be described later in detail.

The recording head driver 104, the main scanning driver 105, and the sub-scanning driver 106 are drivers for driving the recording head 6, the main scanning motor 8, and the sub-scanning motor 12, respectively.

The FPGA 110 for control cooperates with the CPU 101 to control various operations in the image forming apparatus 100. The FPGA 110 for control includes, for example, a CPU control unit 111, a memory control unit 112, an ink ejection control unit 113, a sensor control unit 114, and a motor control unit 115 as functional components.

The CPU control unit 111 communicates with the CPU 101 to transmit various pieces of information acquired by the FPGA 110 for control to the CPU 101, and inputs the control command output from the CPU 101.

The memory control unit 112 performs memory control so that the CPU 101 can access the ROM 102 or the RAM 103.

The ink ejection control unit 113 controls an operation of the recording head driver 104 corresponding to the control command from the CPU 101 to control the ejection timing of the ink from the recording head 6 driven by the recording head driver 104.

The sensor control unit 114 performs processing on a sensor signal such as an encoder value output from the encoder sensor 13.

The motor control unit 115 controls an operation of the main scanning driver 105 corresponding to the control command from the CPU 101 to control the main scanning motor 8 driven by the main scanning driver 105, and controls movement of the carriage 5 in the main-scanning direction. The motor control unit 115 also controls an operation of the sub-scanning driver 106 corresponding to the control command from the CPU 101 to control the sub-scanning motor 12 driven by the sub-scanning driver 106, and controls movement of the printing medium P on the platen 16 in the sub-scanning direction.

The units described above are examples of a control function implemented by the FPGA 110 for control. In addition, various control functions may be implemented by the FPGA 110 for control. For example, the FPGA 110 for control may be configured to implement the function of the colorimetry starting control unit 150 described above implemented by a computer program executed by the CPU 101. All or part of the control functions described above may be implemented by a computer program executed by the CPU 101 or another general-purpose CPU. Alternatively, part of the control functions described above may be implemented by dedicated hardware such as another FPGA different from the FPGA 110 for control or an application specific integrated circuit (ASIC).

The recording head 6 is driven by the recording head driver 104 the operation of which is controlled by the CPU 101 and the FPGA 110 for control, and ejects the ink to the printing medium P on the platen 16 to print the image. Specifically, in performing calibration of the image forming apparatus 100, the recording head 6 ejects the ink on the printing medium P corresponding to the control by the CPU 101 and the FPGA 110 for control to print the test pattern in which a large number of patches 200 are arranged as colorimetric objects (printing unit).

As described above, in performing calibration of the image forming apparatus 100, the colorimetric camera 20 captures the image of each patch 200 included in the test pattern together with the reference chart 400, and calculates the colorimetric value of the patch 200 (a color specification value in the standard color space, for example, an L*a*b* value in an L*a*b* color space (hereinafter, L*a*b* is referred to as "Lab")) based on an RGB value of the patch 200 obtained from the captured image and an RGB value of each reference patch of the reference chart 400. The colorimetric value of the patch 200 calculated by the colorimetric camera 20 is transmitted to the CPU 101 via the FPGA 110 for control. A specific example of a colorimetric method for the patch 200 according to the embodiment will be described later in detail.

As described above, the color adjustment of the image forming apparatus 100 may be performed by using the RGB value of the patch 200. In this case, the colorimetric camera 20 captures the image of each patch 200 included in the test pattern for the color adjustment together with the reference chart 400 by the two-dimensional image sensor 27, and performs processing to correct an error due to a change in the illumination light source 30 with respect to the RGB value of the patch 200 obtained from a taken image, by using the RGB value of each reference patch of the reference chart 400. The corrected RGB value of the patch 200 is sent from the colorimetric camera 20 to the CPU 101 through the control FPGA 110, for example. The CPU 101 adjusts a parameter or the like for controlling the ejection amount of the ink by using the RGB value, to thereby adjust the amount of ink ejected from the recording head 6 to the printing medium P.

The encoder sensor 13 outputs the encoder value obtained by detecting a mark of the encoder sheet 14 to the FPGA 110 for control. This encoder value is transmitted from the FPGA 110 for control to the CPU 101 and used for calculating the position or speed of the carriage 5, for example. The CPU 101 generates and outputs a control command for controlling the main scanning motor 8 based on the position and the speed of the carriage 5 calculated from the encoder value.

Colorimetry Starting Control Unit

Next, the following describes details about processing performed by the colorimetry starting control unit 150 implemented as a function of the CPU 101.

As described above, the image forming apparatus 100 according to the embodiment performs colorimetry on each patch 200 included in the test pattern printed on the printing medium P using the colorimetric camera 20. That is, the sensor unit 26 of the colorimetric camera 20 captures the image of the patch 200 as the colorimetric object, and calculates the colorimetric value of the patch 200 based on the obtained RGB value of the patch 200. In this case, when the ink of the patch 200 is not dried, the RGB value of the patch 200 measured by image capturing is not stabilized, so that a correct colorimetric value cannot be obtained. Accordingly, in the image forming apparatus 100 according to the embodiment, the colorimetry starting control unit 150 is arranged in the CPU 101, and the colorimetry starting control unit 150 is caused to start colorimetry of each patch 200 included in the test pattern at an appropriate timing to obtain the correct colorimetric value.

FIG. 7 is a diagram illustrating a temporal change in the RGB value measured by capturing an image of an arbitrary patch 200 included in the test pattern with the colorimetric camera 20. The RGB value is color information represented by an output value (luminance value) output from the sensor unit 26 for each channel of RGB. In the drawing, a graph indicated by a solid line represents an output value (luminance value) of an R channel output from the sensor unit 26, a graph indicated by an alternate long and short dash line represents a sensor output value (luminance value) of a G channel, and a graph indicated by a dashed line represents a sensor output value (luminance value) of a B channel.

When the patch 200 is printed by ejecting the ink on the printing medium P, a film thickness of the ink on the printing medium P is reduced as the ink permeates the printing medium P with a lapse of time, so that a density of the ink gradually decreases. Accordingly, the RGB value (luminance value) of the patch 200 measured by using the colorimetric camera 20 increases with a lapse of time as illustrated in FIG. 7. The ink is dried when a certain time elapses, so that the RGB value of the patch 200 is stabilized. This process indicates that the correct colorimetric value of the patch 200 cannot be obtained until the ink of the patch 200 is dried.

FIG. 8 is a diagram listing, in a table, factors that affect the time until the ink of the patch 200 is dried and the RGB value is stabilized (hereinafter, referred to as a stabilizing time). A variation is caused in the stabilizing time for each patch 200 included in the test pattern due to the various factors illustrated in FIG. 8. Accordingly, in the technique disclosed in Japanese Patent Application Laid-open No. 2010-241061, drying time for the ink is calculated in advance for each combination of these factors, and the drying time is set corresponding to a combination that meets a condition in a case of printing (printing condition). However, the combinations described above are widely diverse, so that it is actually difficult to calculate the drying time for all the combinations. Due to this, correct drying time cannot be set and colorimetry cannot be started at an appropriate timing in some cases.

In contrast, in the image forming apparatus 100 according to the embodiment, the colorimetry starting control unit 150 in the CPU 101 performs processing described below, so that colorimetry of each patch 200 included in the test pattern is started at an appropriate timing and the correct colorimetric value can be obtained.

The colorimetry starting control unit 150 is called when the printing of the test pattern is finished, and moves the colorimetric camera 20 to a position opposite to a predetermined patch 200 (hereinafter, this patch 200 is referred to as a representative patch $P_{rep}$) among a large number of patches 200 included in the test pattern.

Next, the colorimetry starting control unit 150 measures the RGB value (color information) of the representative patch $P_{rep}$ using the colorimetric camera 20, and holds the measurement result. Thereafter, the colorimetry starting control unit 150 waits for a predetermined time (t seconds). When t seconds elapse, the colorimetry starting control unit 150 measures the RGB value of the representative patch $P_{rep}$ again using the colorimetric camera 20. The colorimetry starting control unit 150 then obtains a variation amount of the RGB value of the representative patch $P_{rep}$ from a difference between a newly obtained measurement result and the measurement result obtained t seconds before, and determines whether the variation amount is equal to or smaller than a predetermined threshold Th.

Herein, the variation amount of the RGB value of the representative patch $P_{rep}$ is assumed to be a change amount of a luminance value of a channel in which the difference in the measurement results is the largest among the channels of RGB, for example. As the threshold Th for the variation amount, for example, a value may be set in advance by which it is assumed there is no variation in the RGB value considering a measurement error.

When the variation amount of the RGB value of the representative patch $P_{rep}$ exceeds the threshold Th, the colorimetry starting control unit 150 holds the measurement result obtained at the point of time, and measures the RGB value of the representative patch $P_{rep}$ again after t seconds elapses. The colorimetry starting control unit 150 then obtains the variation amount of the RGB value of the representative patch $P_{rep}$ again using the same method as described above, and determines whether the variation amount is equal to or smaller than the threshold Th again.

The colorimetry starting control unit 150 repeats the processes described above until the variation amount of the RGB value of the representative patch $P_{rep}$ becomes equal to or smaller than the threshold Th. After the variation amount of the RGB value of the representative patch $P_{rep}$ is equal to or smaller than the threshold Th, the colorimetry starting control unit 150 outputs a control command to start colorimetry of each patch 200 included in the test pattern.

Corresponding to the control command from the colorimetry starting control unit 150, colorimetry of each patch 200 is started using the colorimetric camera 20. When colorimetry is started, the colorimetric camera 20 successively moves to a position opposite to each patch 200 included in the test pattern and captures the image of each patch 200. Then the colorimetric value of each patch 200 is calculated from the RGB value of each patch 200 obtained by image capturing. In this case, the RGB value of the representative patch $P_{rep}$ is already acquired, so that imaging of the representative patch $P_{rep}$ can be omitted.

Figures 9A, 9B:
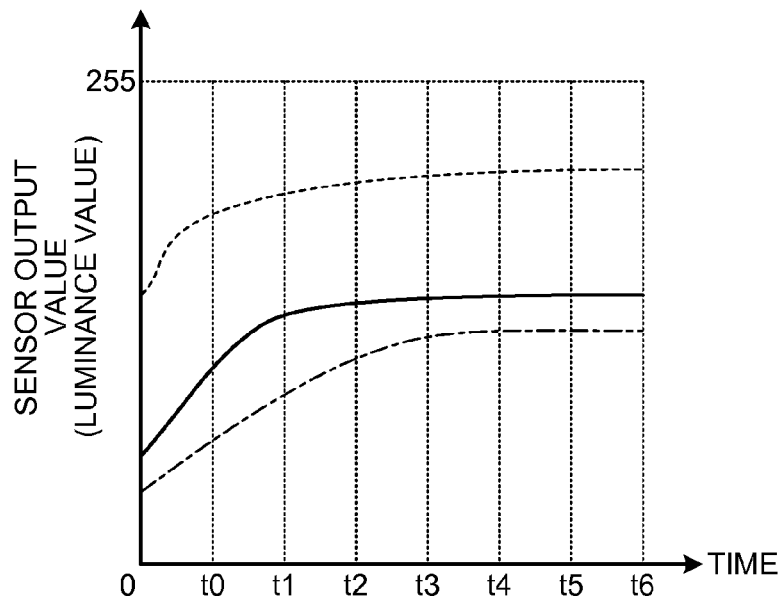
FIGS. 9A and 9B are diagrams for explaining processing in a colorimetry starting control unit.

FIGS. 9A and 9B are diagrams for explaining processing in the colorimetry starting control unit 150. FIG. 9A illustrates a temporal change in the RGB value of the representative patch $P_{rep}$. FIG. 9B illustrates RGB values of the representative patch $P_{rep}$ measured at points of time 0 to t6 in FIG. 9A. In FIG. 9A, a graph indicated by a solid line represents the sensor output value (luminance value) of the R channel, a graph indicated by an alternate long and short dash line represents the sensor output value (luminance value) of the G channel, and a graph indicated by a dashed line represents the sensor output value (luminance value) of the B channel.

When the test pattern is printed on the printing medium P, the colorimetry starting control unit 150 measures the RGB values of the representative patch $P_{rep}$ included in the test pattern at the points of time 0 to t6 using the colorimetric camera 20, and determines whether the variation amount of the RGB value is equal to or smaller than the threshold Th. In the example illustrated in FIGS. 9A and 9B, the variation amount of the RGB value between the points of time t5 and t6 is equal to or smaller than the threshold Th. Accordingly, the colorimetry starting control unit 150 outputs a control command to start colorimetry of each patch 200 included in the test pattern at the point of time t6.

The representative patch $P_{rep}$ as a measurement target can be determined in advance corresponding to a type of ink to be used and a use amount thereof from among the patches 200 included in the test pattern, for example.

The stabilizing time in which the ink is dried and the RGB value is stabilized depends on the various factors illustrated in FIG. 8. However, under a condition in which a type of the printing medium P and a temperature or humidity at the time of printing are the same, the length of the stabilizing time basically depends on the type of the ink to be used and the use amount thereof. Accordingly, a patch the stabilizing time of which is expected to be the longest is determined as the representative patch $P_{rep}$ depending on the type of the ink to be used and the use amount thereof from among the patches 200 included in the test pattern. Due to this, when the RGB value of the representative patch $P_{rep}$ is stabilized, the RGB values of all other patches 200 included in the test pattern are assumed to be stabilized, so that colorimetry of each patch 200 can be started at an appropriate timing.

A patch 200 that is printed at a relatively late timing among the patches 200 included in the test pattern may be assumed to be the representative patch $P_{rep}$.

Figure 10:
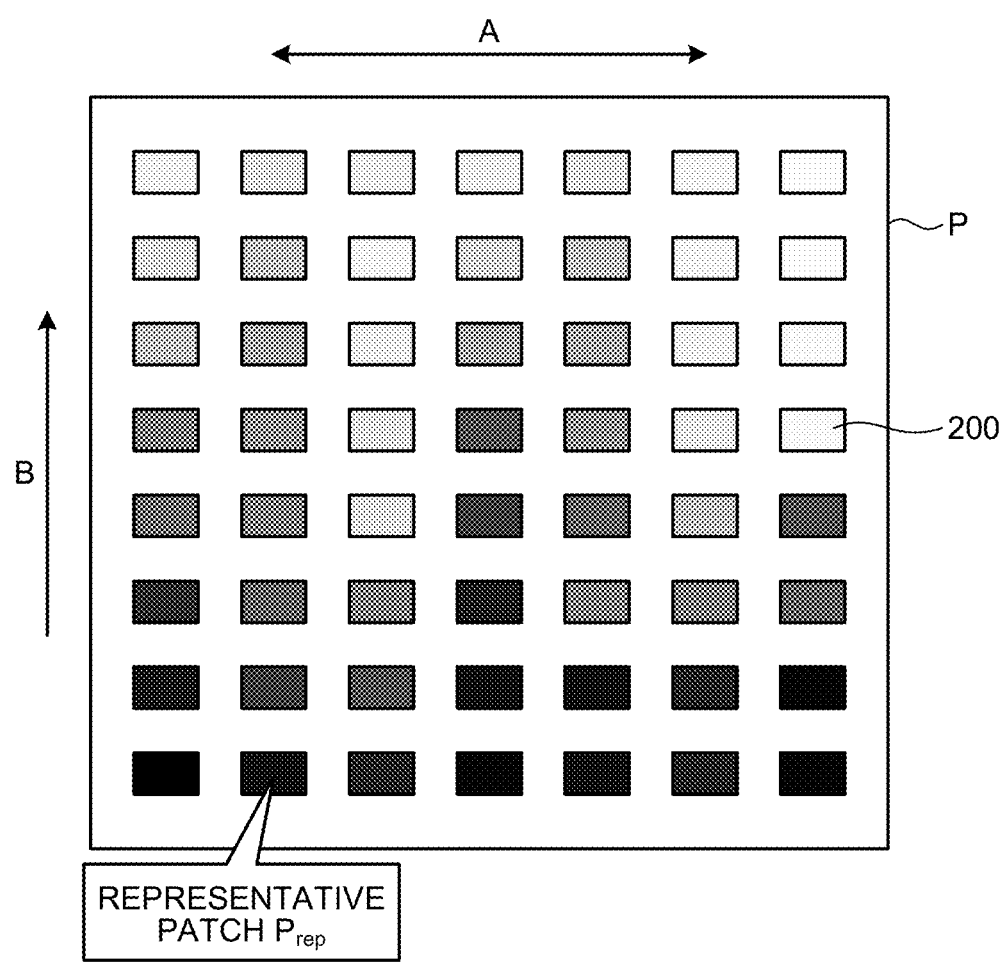
FIG. 10 is a diagram illustrating an example of a test pattern printed on a printing medium.

FIG. 10 is a diagram illustrating an example of the test pattern printed on the printing medium P. As described above, the test pattern is printed by intermittently conveying the printing medium P in the sub-scanning direction (the arrow B direction in the drawing) and ejecting the ink from the recording head 6 to the printing medium P while moving the carriage 5 in the main-scanning direction (the arrow A direction in the drawing) during when the conveyance of the printing medium P in the sub-scanning direction is stopped. Accordingly, among the large number of patches 200 included in the test pattern, a patch 200 positioned ahead of the conveying direction (sub-scanning direction) of the printing medium P is printed at an earlier timing. In the test pattern exemplified in FIG. 10, the patches 200 in upper arrays are printed at a relatively early timing, and the patches 200 in lower arrays are printed at a relatively late timing.

Among the patches 200 included in the test pattern, the ink is dried earlier in the patch 200 printed at a relatively early timing than that in the patch 200 printed at a relatively late timing. Accordingly, the patch 200 printed at a relatively late timing (the patch in the lowest array in the example of FIG. 10) is determined as the representative patch $P_{rep}$. Due to this, when the RGB value of the representative patch $P_{rep}$ is stabilized, the RGB value of the other patch 200 printed at a relatively early timing can be assumed to be stabilized, so that colorimetry of each patch 200 can be started at an appropriate timing.

When the order of colorimetry performed on each patch 200 included in the test pattern is the same as the order of printing each patch (when colorimetry is sequentially performed from the patch 200 in the uppermost array in the example of FIG. 10), colorimetry of each patch 200 included in the test pattern may be started before the RGB value of the representative patch $P_{rep}$ is stabilized. That is, assuming that tx represents the timing at which the RGB value of the representative patch $P_{rep}$ (the patch 200 in the lowermost array in the example of FIG. 10) is stabilized and T represents acceleration time that is determined corresponding to time required for printing all the patches 200 included in the test pattern or time required for performing colorimetry, colorimetry may be started at the timing of tx−T. Due to this, the standby time until colorimetry is started can be shortened.

In this case, the acceleration time T may be set to time obtained by adding a predetermined margin to the time required for printing when the time required for performing colorimetry is longer than the time required for printing all the patches 200. When the time required for performing colorimetry is shorter than the time required for printing all the patches 200, the time required for performing colorimetry to which a predetermined margin is added may be set as the acceleration time T.

To start colorimetry at the timing of tx−T, the threshold Th for the RGB value of the representative patch $P_{rep}$ may be relieved. That is, the threshold Th may be set to a value such that the variation amount of the RGB value of the representative patch $P_{rep}$ at the timing of tx−T is equal to or smaller than the threshold Th.

Figure 11:
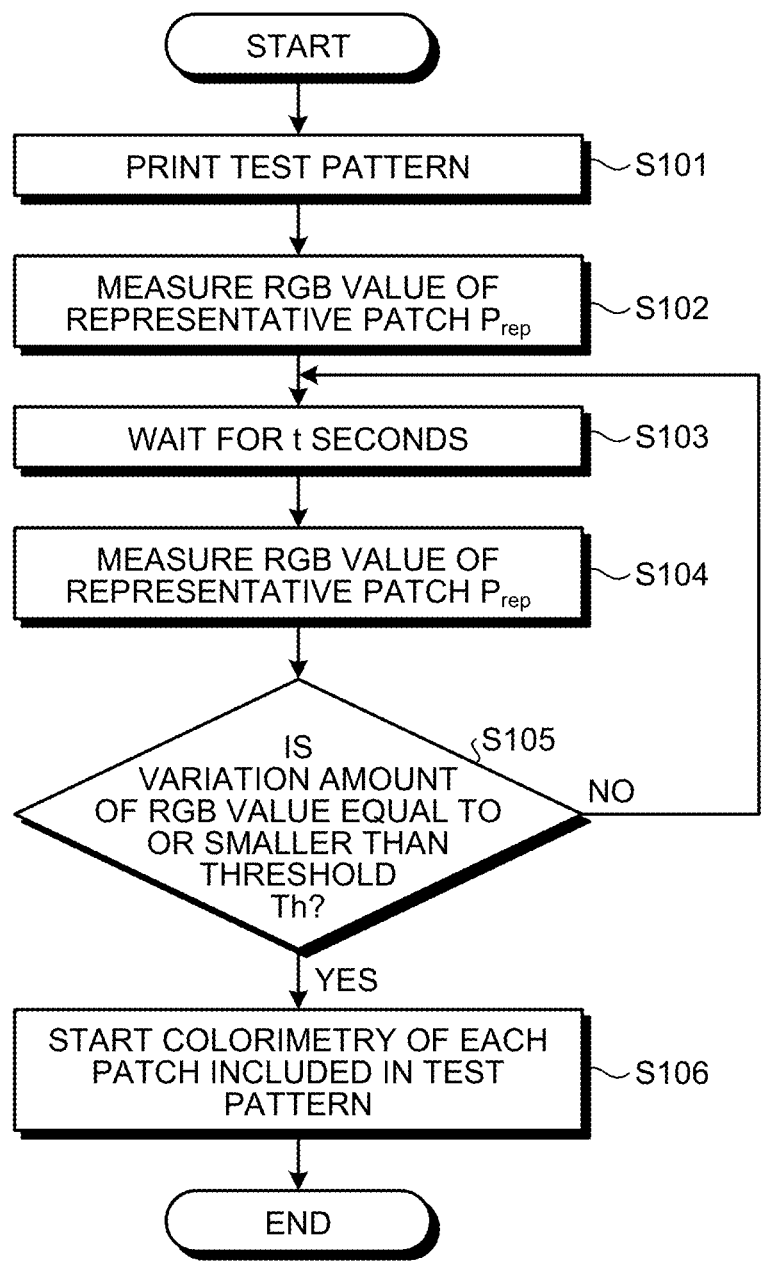
FIG. 11 is a flowchart illustrating a processing procedure for performing colorimetry on each patch included in the test pattern.

FIG. 11 is a flowchart illustrating a processing procedure for performing colorimetry on each patch 200 included in the test pattern in the image forming apparatus 100 according to the embodiment.

First, the test pattern in which the patches 200 as colorimetric objects are arrayed is printed on the printing medium P (Step S101).

When the test pattern is printed, the colorimetry starting control unit 150 moves the colorimetric camera 20 to a position opposite to the representative patch $P_{rep}$, measures the RGB value of the representative patch $P_{rep}$ using the colorimetric camera 20, and holds the measurement result (Step S102).

Thereafter, the colorimetry starting control unit 150 waits for t seconds (Step S103). When t seconds have elapsed, the colorimetry starting control unit 150 measures the RGB value of the representative patch $P_{rep}$ again using the colorimetric camera 20 (Step S104). The colorimetry starting control unit 150 then obtains a variation amount of the RGB value from a difference between the RGB value of the representative patch $P_{rep}$ measured at Step S102 and the RGB value measured at Step S104, and determines whether the variation amount of the RGB value is equal to or smaller than the predetermined threshold Th (Step S105).

As a result of the determination at Step S105, if the variation amount of the RGB value of the representative patch $P_{rep}$ exceeds the threshold Th (No at Step S105), the colorimetry starting control unit 150 returns to Step S103 and repeats the subsequent processing. On the other hand, as a result of the determination at Step S105, if the variation amount of the RGB value of the representative patch $P_{rep}$ is equal to or smaller than the threshold Th (Yes at Step S105), the colorimetry starting control unit 150 outputs a control command to start colorimetry of each patch 200 included in the test pattern, and starts colorimetry of each patch 200 using the colorimetric camera 20 (Step S106).

In the embodiment, one of the patches 200 included in the test pattern is assumed to be the representative patch $P_{rep}$. Alternatively, a plurality of representative patches $P_{rep}$ may be set. In this case, the colorimetry starting control unit 150 may measure the RGB value (color information) of each of the representative patches $P_{rep}$ over time, and may start colorimetry of each patch 200 included in the test pattern after all variation amounts of the RGB values of the representative patches $P_{rep}$ become equal to or smaller than the threshold Th.

In the embodiment, the RGB value of the representative patch $P_{rep}$ is measured at regular intervals (every t seconds). However, the measurement is not necessarily performed at regular intervals. For example, the interval for measuring the RGB value of the representative patch $P_{rep}$ may be changed corresponding to the variation amount of the RGB value of the representative patch $P_{rep}$.

Figure 12:
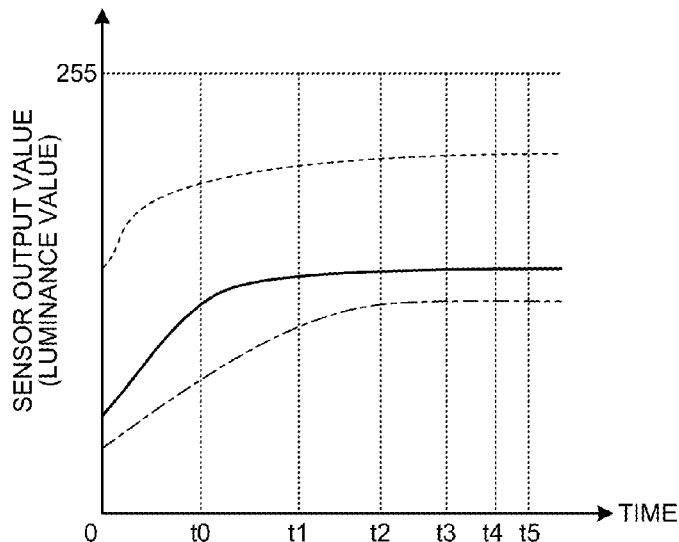
FIG. 12 is a diagram for explaining an example of shortening an interval for measuring the RGB value of a representative patch as a variation amount of the RGB value of the representative patch decreases.

FIG. 12 is a diagram for explaining an example of shortening an interval for measuring the RGB value of the representative patch $P_{rep}$ as the variation amount of the RGB value of the representative patch $P_{rep}$ decreases. In the drawing, a graph indicated by a solid line represents the sensor output value (luminance value) of the R channel, a graph indicated by an alternate long and short dash line represents the sensor output value (luminance value) of the G channel, and a graph indicated by a dashed line represents the sensor output value (luminance value) of the B channel. In the drawing, 0 to t5 indicate the timing for measuring the RGB value of the representative patch $P_{rep}$. As illustrated in FIG. 12, by shortening the interval for measuring the RGB value of the representative patch $P_{rep}$ as the variation amount of the RGB value of the representative patch $P_{rep}$ decreases, the timing at which the RGB value of the representative patch $P_{rep}$ is stabilized can be detected more correctly.

In the above description, assuming that the color adjustment of the image forming apparatus 100 is performed by using the colorimetric value of each patch 200 included in the test pattern, colorimetry of each patch 200 is started after the variation amount of the RGB value of the representative patch Prep becomes equal to or smaller than the threshold Th. In contrast, when the color adjustment of the image forming apparatus 100 is performed by using the RGB values of the patches 200 instead of the colorimetric values, it is preferable to start the color adjustment using the RGB value of each patch 200 after the variation amount of the RGB value of the representative patch Prep becomes equal to or smaller than the threshold Th. That is, it is preferable to acquire the RGB value of each patch 200 by the colorimetric camera 20 and perform the color adjustment of the image forming apparatus 100 by using the acquired RGB values after the variation amount of the RGB value of the representative patch Prep becomes equal to or smaller than the threshold Th.

Configuration of Control Mechanism of Colorimetric Camera

Figure 13:
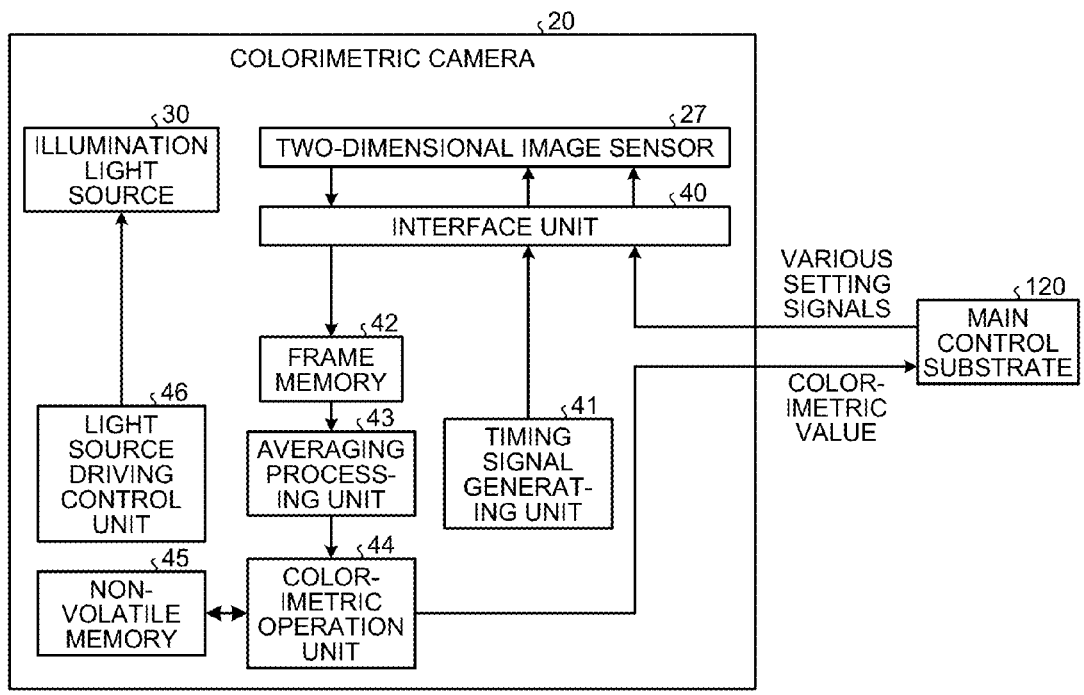
FIG. 13 is a control block diagram of the colorimetric camera.

Next, the following specifically describes a configuration example of a control mechanism of the colorimetric camera 20 with reference to FIG. 13. FIG. 13 is a control block diagram of the colorimetric camera 20.

As illustrated in FIG. 13, the colorimetric camera 20 includes an interface unit 40, a timing signal generating unit 41, a frame memory 42, an averaging processing unit 43, a colorimetric operation unit 44, a nonvolatile memory 45, and a light source driving control unit 46 in addition to the two-dimensional image sensor 27 and the illumination light source 30. These components are mounted, for example, on the substrate 22 configuring the upper surface part of the housing 23 of the colorimetric camera 20.

The two-dimensional image sensor 27 converts light incident through the imaging forming lens 28 into an electric signal, and outputs image data obtained by capturing an image of a capturing target region of the sensor unit 26. The two-dimensional image sensor 27 incorporates a function of AD-converting an analog signal obtained through photoelectric conversion into digital image data and outputting the image data after performing various image processing such as shading correction, white balance correction, γ correction, and format conversion on the image data. Part or all of the various pieces of image processing on the image data may be performed outside the two-dimensional image sensor 27.

The interface unit 40 is an interface for outputting the image data from the two-dimensional image sensor 27 and inputting various setting signals transmitted from the main control substrate 120 of the image forming apparatus 100 and a timing signal generated by the timing signal generating unit 41 to the two-dimensional image sensor 27. The various setting signals include a signal for setting an operation mode of the two-dimensional image sensor 27 and a signal for setting an imaging condition such as shutter speed or an AGC gain.

The timing signal generating unit 41 generates a timing signal that controls the timing for starting imaging by the two-dimensional image sensor 27, and inputs the timing signal to the two-dimensional image sensor 27 via the interface unit 40. The timing for measuring the RGB value of the representative patch $P_{rep}$ described above is controlled by the timing signal generated by the timing signal generating unit 41.

The frame memory 42 temporarily stores the image data output from the two-dimensional image sensor 27.

The averaging processing unit 43 averages pixel data in a region of the patch 200 as the colorimetric object based on the image data stored in the frame memory 42, also averages pixel data in a region of each reference patch of the reference chart 400, and outputs each of the averaged values to the colorimetric operation unit 44 as the RGB value of the colorimetric object and the RGB value of each reference patch of the reference chart 50. In measuring the RGB value of the representative patch $P_{rep}$ described above, the RGB value of the representative patch $P_{rep}$ obtained by the averaging processing unit 43 is transmitted to the CPU 101 on the main control substrate 120.

The colorimetric operation unit 44 calculates the colorimetric value of the patch 200 based on the RGB value of the patch 200 obtained through the processing performed by the averaging processing unit 43 and the RGB value of each reference patch of the reference chart 400. The colorimetric value calculated by the colorimetric operation unit 44 is transmitted to the CPU 101 on the main control substrate 120. A specific example of the processing performed by the colorimetric operation unit 44 will be described later in detail.

The nonvolatile memory 45 stores various pieces of data required for calculating the colorimetric value of the patch 200 by the colorimetric operation unit 44.

The light source driving control unit 46 generates a light source driving signal for driving the illumination light source 30 and supplies the light source driving signal to the illumination light source 30.

Specific Example of Colorimetric Method for Patch

Next, the following describes a specific example of a colorimetric method for the patch 200 by the image forming apparatus 100 according to the embodiment in detail with reference to FIGS. 14 to 20. The colorimetric method described below includes preprocessing performed when the image forming apparatus 100 is in an initial state (caused to be in the initial state due to manufacturing or an overhaul), and colorimetric processing performed in performing calibration of in the image forming apparatus 100.

Figure 14:
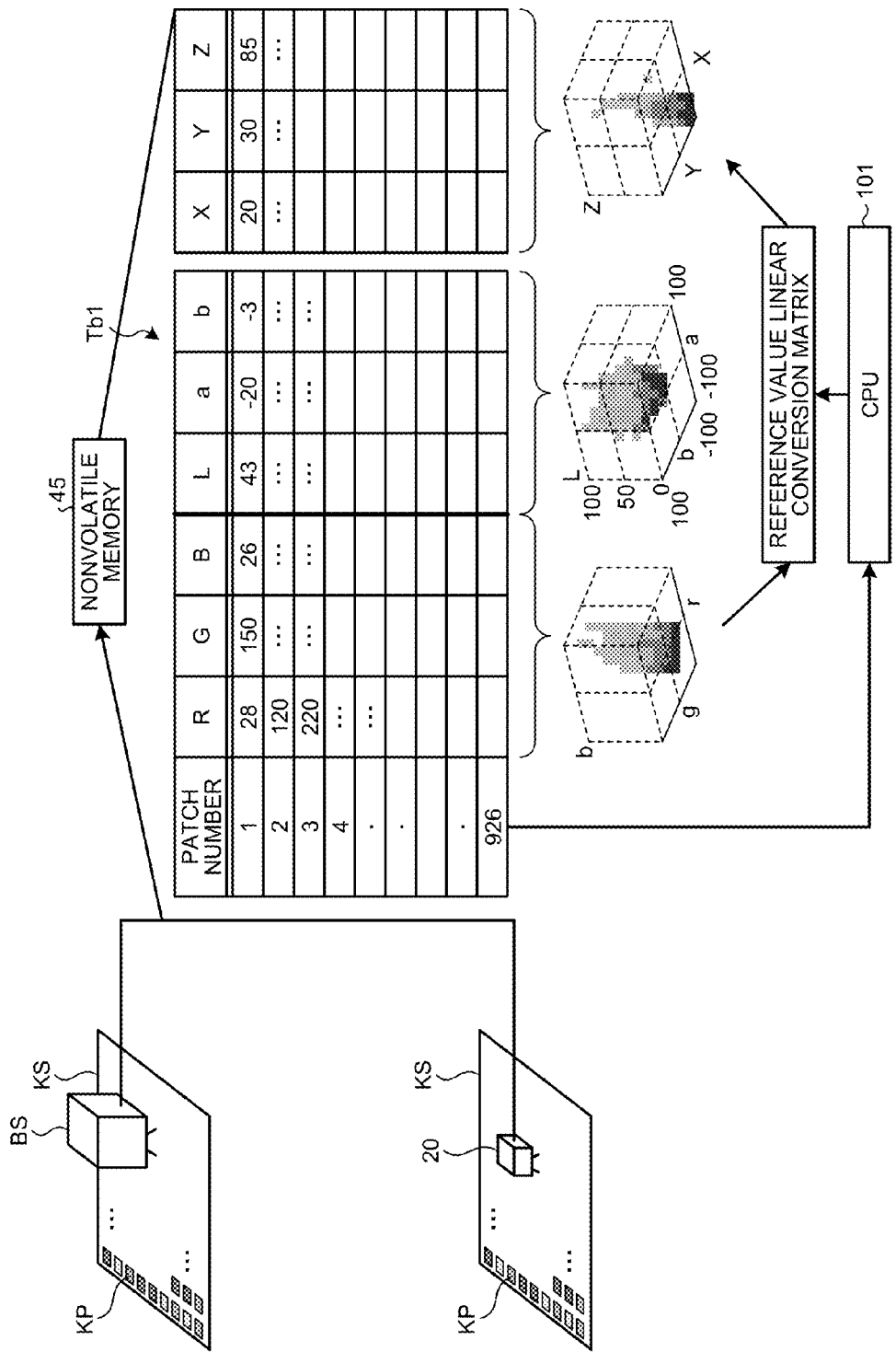
FIG. 14 is a diagram for explaining processing of acquiring a reference colorimetric value and a reference RGB value and processing of generating a reference value linear conversion matrix.

FIG. 14 is a diagram for explaining processing of acquiring a reference colorimetric value and a reference RGB value and processing of generating a reference value linear conversion matrix. The processing illustrated in FIG. 14 is performed as the preprocessing. In the preprocessing, used is a reference sheet KS in which a plurality of reference patches KP are arrayed and formed. The reference patch KP in the reference sheet KS is equivalent to the patch of the reference chart 400 included in the colorimetric camera 20.

At least one of an Lab value and an XYZ value as the colorimetric values of the reference patches KP in the reference sheet KS (in the example of FIG. 14, both of the Lab value and the XYZ value) is stored, for example, in a memory table Tb1 provided in the nonvolatile memory 45 mounted on the substrate 22 of the colorimetric camera 20 corresponding to each of patch numbers. The colorimetric value of the reference patch KP is a value that can be obtained in advance through colorimetry using a spectroscope BS and the like. If the colorimetric value of the reference patch KP is already known, the value may be used. Hereinafter, the colorimetric value of the reference patch KP stored in the memory table Tb1 is referred to as a "reference colorimetric value".

Next, the reference sheet KS is set on the platen 16 to control the movement of the carriage 5, and the colorimetric camera 20 captures an image of the reference patches KP in the reference sheet KS as subjects. The RGB values of the reference patches KP obtained through imaging by the colorimetric camera 20 are stored in the memory table Tb1 of the nonvolatile memory 45 corresponding to the patch numbers. That is, the memory table Tb1 stores therein the colorimetric value and the RGB value of each of the reference patches KP arrayed and formed on the reference sheet KS corresponding to the patch number of each reference patch KP. Hereinafter, the RGB value of the reference patch KP stored in the memory table Tb1 is referred to as a "reference RGB value". The reference RGB value is a value reflecting a characteristic of the colorimetric camera 20.

When the reference colorimetric value and the reference RGB value of the reference patch KP are stored in the memory table Tb1 of the nonvolatile memory 45, the CPU 101 of the image forming apparatus 100 generates the reference value linear conversion matrix for mutually converting a pair of the XYZ value and the reference RGB value as the reference colorimetric values of the same patch number, and stores the reference value linear conversion matrix in the nonvolatile memory 45. When only the Lab value is stored as the reference colorimetric value in the memory table Tb1, the reference value linear conversion matrix may be generated after converting the Lab value into the XYZ value using a known conversion expression for converting the Lab value into the XYZ value.

Figure 15:
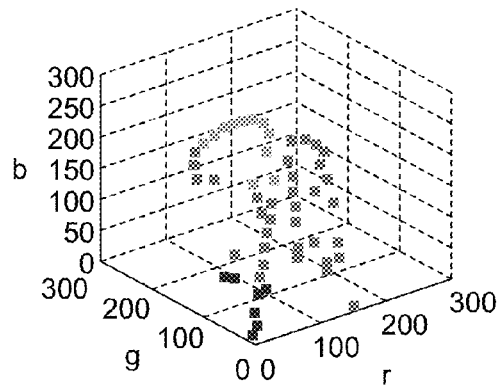
FIG. 15 illustrates an example of an initial reference RGB value.

When the colorimetric camera 20 captures the image of the reference patches KP in the reference sheet KS, the reference chart 400 provided to the colorimetric camera 20 is also captured at the same time. The RGB value of each patch of the reference chart 400 obtained through this imaging is also stored in the memory table Tb1 of the nonvolatile memory 45 corresponding to the patch number. The RGB value of the patch of the reference chart 400 stored in the memory table Tb1 through the preprocessing is referred to as an "initial reference RGB value". FIG. 15 illustrates an example of the initial reference RGB value. In FIG. 15, (a) illustrates a state in which the initial reference RGB value (RdGdBd) is stored in the memory table Tb1, and an initial reference Lab value (Ldadbd) obtained by converting the initial reference RGB value (RdGdBd) into the Lab value and an initial reference XYZ value (XdYdZd) obtained by converting the initial reference RGB value (RdGdBd) into the XYZ value are also stored therein in association with the initial reference RGB value (RdGdBd). In FIG. 15, (b) is a scatter diagram plotting the initial reference RGB value of each patch of the reference chart 400.

After the preprocessing is finished, the image forming apparatus 100 drives the main scanning motor 8, the sub-scanning motor 12, and the recording head 6 under the control by the CPU 101 based on the image data or a print setting input from the outside, intermittently conveys the printing medium P in the sub-scanning direction while moving the carriage 5 in the main-scanning direction, and causes the recording head 6 to eject the ink to print the image on the printing medium P. In this case, an ejection amount of the ink from the recording head 6 may vary due to a characteristic specific to a device or a temporal change. When the ejection amount of the ink is changed, the image is formed with a color different from a color of the image intended by a user, so that color reproducibility is deteriorated. Accordingly, the image forming apparatus 100 performs colorimetric processing for obtaining the colorimetric value of the patch 200 included in a test chart printed on the printing medium P at a predetermined timing for adjusting the color. The image forming apparatus 100 then generates or corrects a device profile based on the colorimetric value of the patch 200 obtained through the colorimetric processing and performs color adjustment based on the device profile to enhance the color reproducibility of an output image.

Figure 16:
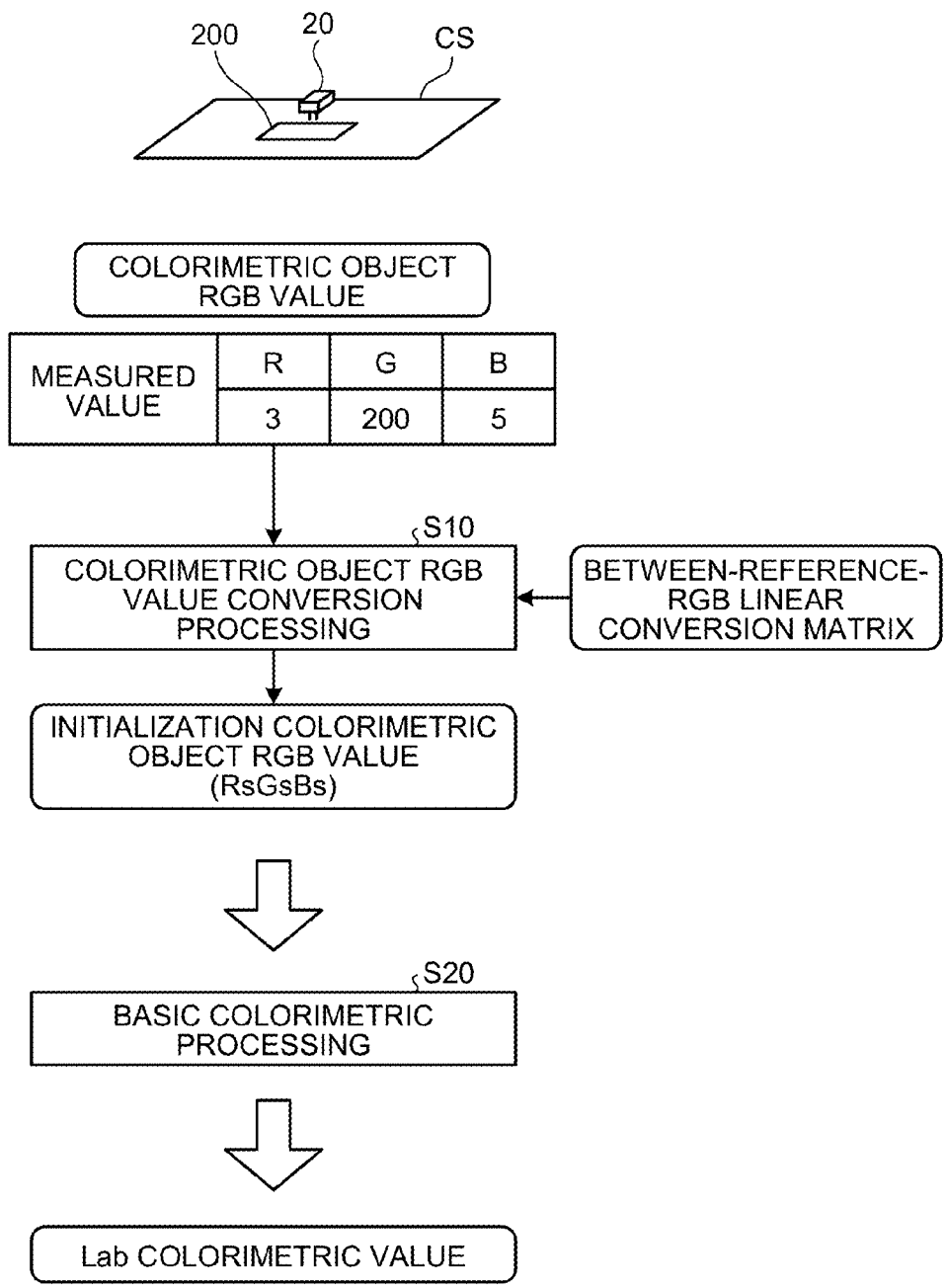
FIG. 16 is a diagram for explaining an outline of colorimetric processing.

FIG. 16 is a diagram for explaining an outline of the colorimetric processing. In performing calibration for adjusting color, the image forming apparatus 100 ejects the ink from the recording head 6 on the printing medium P set on the platen 16 to print the test pattern in which a large number of patches 200 are arranged. Hereinafter, the printing medium P on which the test pattern is printed is referred to as an "adjustment sheet CS". On the adjustment sheet CS, the patch 200 is printed reflecting an output characteristic in calibration of the image forming apparatus 100, particularly, an output characteristic of the recording head 6. The image data for printing the test pattern is stored in the nonvolatile memory 45 and the like in advance.

Next, the image forming apparatus 100 waits until the RGB value of each patch 200 included in the adjustment sheet CS is stabilized due to the function of the colorimetry starting control unit 150 described above. When the RGB value of each patch 200 included in the adjustment sheet CS is stabilized, as illustrated in FIG. 16, the colorimetric camera 20 is sequentially moved to a position opposite to each patch 200 on the adjustment sheet CS to capture an image with the two-dimensional image sensor 27 thereof. Then the RGB value of the patch 200 is obtained from the image data output from the two-dimensional image sensor 27 through the processing performed by the averaging processing unit 43. The two-dimensional image sensor 27 also captures an image of the reference chart 400 together with the patch 200 as the colorimetric object at the same time, so that the RGB value of each patch included in the reference chart 400 can also be obtained. Hereinafter, the RGB value of the patch 200 as the colorimetric object is referred to as a "colorimetric object RGB value", and the RGB value of the patch in the reference chart 400 is referred to as a "reference RGB value in colorimetry (RdsGdsBds)". The "reference RGB value in colorimetry (RdsGdsBds)" is stored in the nonvolatile memory 45 and the like.

The colorimetric operation unit 44 of the colorimetric camera 20 converts the colorimetric object RGB value into the initialization colorimetric object RGB value (RsGsBs) using a between-reference-RGB linear conversion matrix described later (Step S10). The initialization colorimetric object RGB value (RsGsBs) is obtained by eliminating influence, from the colorimetric object RGB value, of a temporal change in the image capturing condition of the colorimetric camera 20 caused in a time period from the initial state in which the preprocessing is performed until the calibration for performing colorimetric processing, for example, a temporal change in the illumination light source 30 or a temporal change in the two-dimensional image sensor 27.

Thereafter, the colorimetric operation unit 44 performs basic colorimetric processing described later on the initialization colorimetric object RGB value (RsGsBs) that is converted from the colorimetric object RGB value (Step S20) to acquire the Lab value being the colorimetric value of the patch 200 as the colorimetric object.

Figure 17:
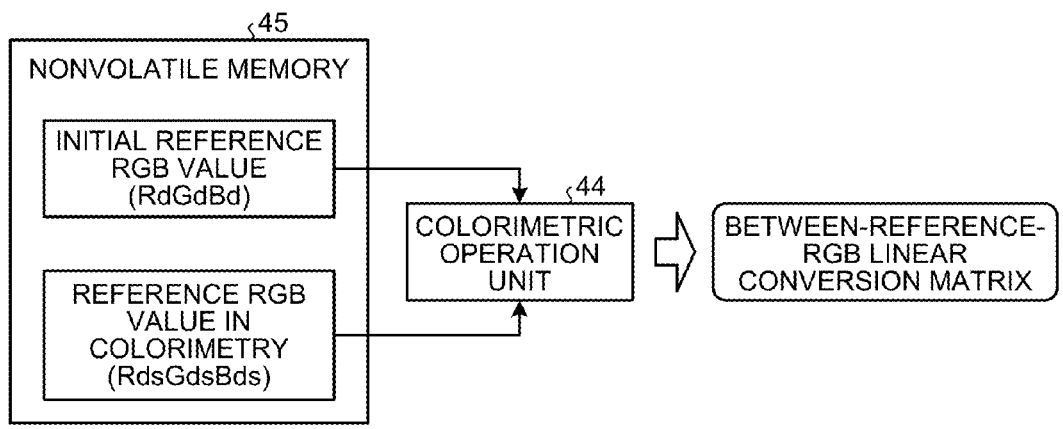
FIG. 17 is a diagram for explaining processing of generating a between-reference-RGB linear conversion matrix.
Figure 18:
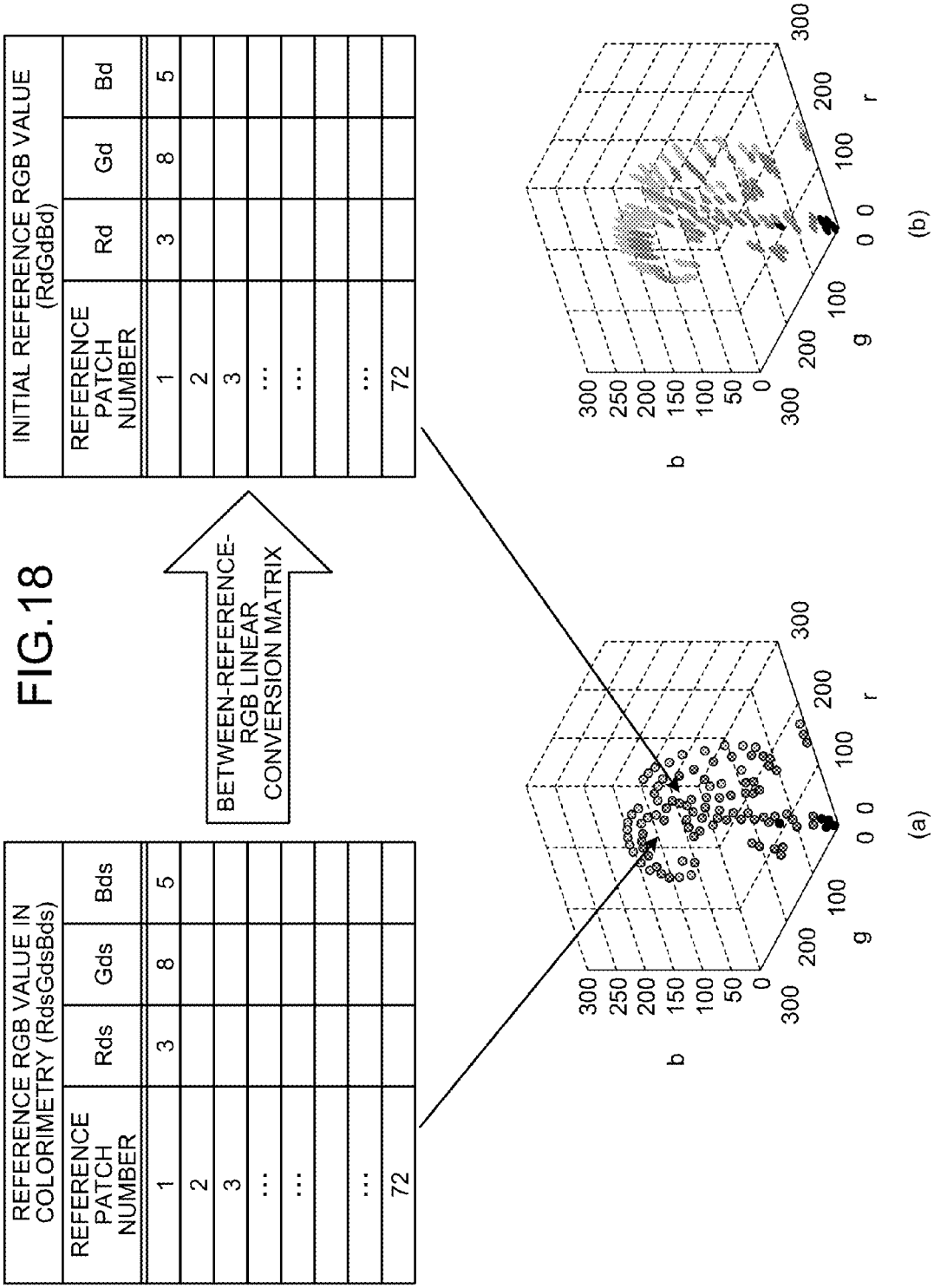
FIG. 18 illustrates a relation between the initial reference RGB value and a reference RGB value in colorimetry.

FIG. 17 is a diagram for explaining processing of generating the between-reference-RGB linear conversion matrix. FIG. 18 illustrates a relation between the initial reference RGB value and the reference RGB value in colorimetry. Before converting the colorimetric object RGB value into the initialization colorimetric object RGB value (RsGsBs) (Step S10), the colorimetric operation unit 44 generates the between-reference-RGB linear conversion matrix used for this conversion. That is, as illustrated in FIG. 17, the colorimetric operation unit 44 reads out, from the nonvolatile memory 45, the initial reference RGB value (RdGdBd) obtained through the preprocessing when the image forming apparatus 100 is in the initial state and the reference RGB value in colorimetry (RdsGdsBds) obtained in the calibration, and generates the between-reference-RGB linear conversion matrix for converting the reference RGB value in colorimetry RdsGdsBds into the initial reference RGB value RdGdBd. The colorimetric operation unit 44 then stores the generated between-reference-RGB linear conversion matrix in the nonvolatile memory 45.

In (a) in FIG. 18, a faint dot is a dot plotting the initial reference RGB value RdGdBd in an rgb space, and a filled dot is a dot plotting the reference RGB value in colorimetry RdsGdsBds in the rgb space. As seen from (a) in FIG. 18, the reference RGB value in colorimetry RdsGdsBds varies from the initial reference RGB value RdGdBd. Although varying directions of these values in the rgb space are substantially the same as illustrated in (b) in FIG. 18, deviating directions are different from each other depending on a hue. As described above, factors that change the RGB value even when the patch in the same reference chart 400 is captured include the temporal change in the illumination light source 30, the temporal change in the two-dimensional image sensor 27, and the like.

In this way, when the colorimetric value is obtained using the colorimetric object RGB value obtained by capturing an image of the patch 200 in a state in which the RGB value obtained through imaging by the colorimetric camera 20 is varied, an error may be caused in the colorimetric value by an variation amount. Accordingly, the between-reference-RGB linear conversion matrix for converting the reference RGB value in colorimetry RdsGdsBds into the initial reference RGB value RdGdBd is obtained using an estimation method such as a method of least squares between the initial reference RGB value RdGdBd and the reference RGB value in colorimetry RdsGdsBds, the colorimetric object RGB value obtained by capturing an image of the patch 200 with the colorimetric camera 20 is converted into the initialization colorimetric object RGB value RsGsBs using the between-reference-RGB linear conversion matrix, and the basic colorimetric processing described later is performed on the converted initialization colorimetric object RGB value RsGsBs to accurately acquire the colorimetric value of the patch 200 as the colorimetric object.

The between-reference-RGB linear conversion matrix is not limited to a first-order matrix but may be a higher-order nonlinear matrix. When non-linearity is high between the rgb space and an XYZ space, conversion accuracy may be improved by using the high-order matrix.

As described above, the colorimetric operation unit 44 converts the colorimetric object RGB value obtained by capturing an image of the patch 200 into the initialization colorimetric object RGB value (RsGsBs) using the between-reference-RGB linear conversion matrix (Step S10), and then performs the basic colorimetric processing at Step S20 on the initialization colorimetric object RGB value (RsGsBs).

FIGS. 19 and 20 are diagrams for explaining the basic colorimetric processing. First, the colorimetric operation unit 44 reads out the reference value linear conversion matrix generated in the preprocessing and stored in the nonvolatile memory 45, converts the initialization colorimetric object RGB value (RsGsBs) into a first XYZ value using the reference value linear conversion matrix, and stores the first XYZ value in the nonvolatile memory 45 (Step S21). FIG. 19 illustrates an example in which the initialization colorimetric object RGB value (3, 200, 5) is converted into the first XYZ value (20, 80, 10) using the reference value linear conversion matrix.

Next, the colorimetric operation unit 44 converts the first XYZ value that is converted from the initialization colorimetric object RGB value (RsGsBs) at Step S21 into a first Lab value using a known conversion expression, and stores the first Lab value in the nonvolatile memory 45 (Step S22). FIG. 19 illustrates an example in which the first XYZ value (20, 80, 10) is converted into the first Lab value (75, −60, 8) using the known conversion expression.

Next, the colorimetric operation unit 44 searches a plurality of reference colorimetric values (Lab values) stored in the memory table Tb1 of the nonvolatile memory 45 in the preprocessing, and selects a group of a plurality of patches (neighboring color patches) each of which having the reference colorimetric value (Lab value) close to the first Lab value in an Lab space among the reference colorimetric values (Lab values) (Step S23). As the method for selecting the closer patch, for example, employed is a method for calculating a distance between the first Lab value and each of all the reference colorimetric values (Lab values) stored in the memory table Tb1, and selecting a plurality of patches each of which having the Lab value close to the first Lab value (in FIG. 19, the hatched Lab value).

Next, as illustrated in FIG. 20, the colorimetric operation unit 44 takes out the RGB value (reference RGB value) and the XYZ value paired with the Lab value for each of the neighboring color patches selected at Step S23 with reference to memory table Tb1, and selects a combination of the RGB value and the XYZ value from among the RGB values and the XYZ values (Step S24). The colorimetric operation unit 44 then obtains a selected RGB value linear conversion matrix for converting the RGB value of the selected combination (selected group) into the XYZ value using a method of least squares and the like, and stores the obtained selected RGB value linear conversion matrix in the nonvolatile memory 45 (Step S25).

Next, the colorimetric operation unit 44 converts the initialization colorimetric object RGB value (RsGsBs) into a second XYZ value using the selected RGB value linear conversion matrix generated at Step S25 (Step S26). The colorimetric operation unit 44 then converts the second XYZ value obtained at Step S26 into a second Lab value using the known conversion expression (Step S27), and sets the obtained second Lab value as a final colorimetric value of the patch 200 as the colorimetric object. The image forming apparatus 100 generates or corrects the device profile based on the colorimetric value obtained in the colorimetric processing described above, and performs color adjustment based on the device profile to enhance color reproducibility of the output image.

The colorimetric camera 20 described above is configured to provide the reference chart 400 to the housing 23 and image the patch 200 as the colorimetric object and the reference chart 400 at the same time using the two-dimensional image sensor 27 of the sensor unit 26. However, as described above, the initial reference RGB value and the reference RGB value in colorimetry obtained by capturing an image of the reference chart 400 are used for eliminating the influence, from the colorimetric object RGB value obtained by capturing an image of the patch 200 as the colorimetric object, of the temporal change in the image capturing condition of the colorimetric camera 20, for example, the temporal change in the illumination light source 30 or the temporal change in the two-dimensional image sensor 27. That is, the initial reference RGB value and the reference RGB value in colorimetry obtained by capturing the image of the reference chart 400 are used for calculating the between-reference-RGB linear conversion matrix described above and converting the colorimetric object RGB value into the initialization colorimetric object RGB value (RsGsBs) using the between-reference-RGB linear conversion matrix.

Accordingly, when the temporal change in the image capturing condition of the colorimetric camera 20 is negligible with respect to required colorimetric accuracy, the colorimetric value of the patch 200 may be calculated using the colorimetric camera 20 not including the reference chart 400. Alternatively, the colorimetric value of the patch 200 can be calculated using a reflective colorimetric device of simple configuration including a light source and a plurality of light receiving elements having sensitivity for each color instead of the colorimetric camera 20. In this case, the processing of converting the colorimetric object RGB value into the initialization colorimetric object RGB value (Step S10 in FIG. 16) is not performed, and the basic colorimetric processing (Step S20 in FIGS. 16, 19, and 20) is performed on the colorimetric object RGB value.

Specific Example of Reflective Colorimetric Device

Figure 21A:
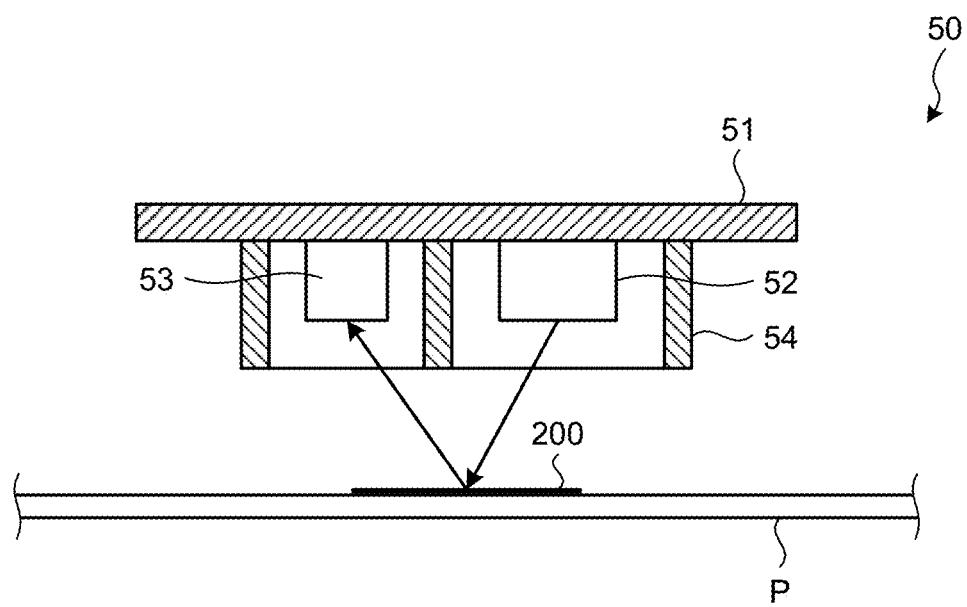
FIG. 21A is a vertical cross-sectional view of a reflective colorimetric device.
Figure 21B:
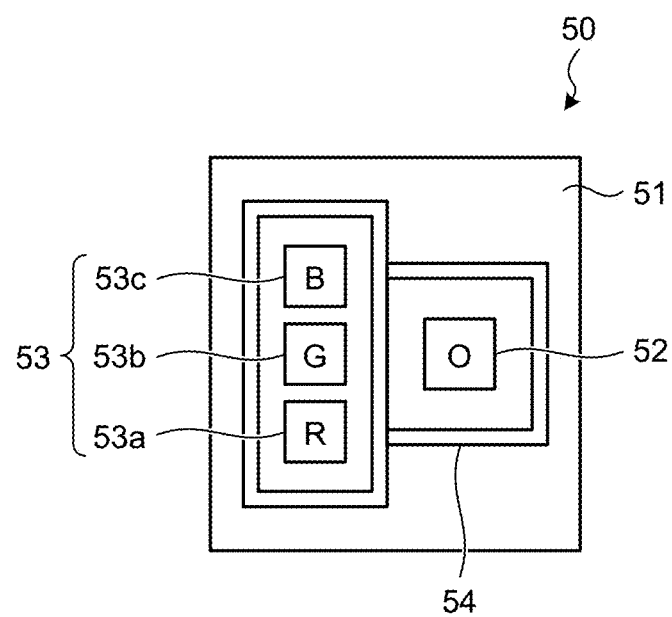
FIG. 21B is a bottom view of the reflective colorimetric device.

FIGS. 21A and 21B are diagrams illustrating an example of a mechanical configuration of a reflective colorimetric device 50. FIG. 21A is a vertical cross-sectional view of the reflective colorimetric device 50. FIG. 21B is a bottom view of the reflective colorimetric device 50.

As illustrated in FIG. 21A, the reflective colorimetric device 50 includes an illumination light source 52, a light receiving unit 53, and a light shielding wall 54 mounted on a substrate 51 being fixed to the carriage 5. The illumination light source 52 is configured with an LED, for example. The light receiving unit 53 is configured by combining a plurality of light receiving elements 53*a*, 53*b*, and 53*c* each of which has different spectral sensitivity (sensitivity of RGB). In the example of FIG. 21B, the light receiving unit 53 is configured by combining the light receiving element 53*a* having high sensitivity of R, the light receiving element 53*b* having high sensitivity of G, and the light receiving element 53*c* having high sensitivity of B. In addition to these light receiving elements 53*a*, 53*b*, and 53*c*, a light receiving element having spectral sensitivity of another color such as gray, cyan, and orange may be further combined to configure the light receiving unit 53.

As illustrated by the arrow in FIG. 21A, the reflective colorimetric device 50 irradiates the patch 200 printed on the printing medium P with illumination light from the illumination light source 52, and makes the light reflected by the patch 200 incident on the light receiving unit 53 to acquire the color information of the patch 200. The light shielding wall 54 is arranged on the substrate 51 so as to surround each of the illumination light source 52 and the light receiving unit 53, and has a function of blocking influence of external light and preventing the illumination light from the illumination light source 52 from directly being incident on the light receiving unit 53 (blocking stray light).

As described above in detail with specific examples, in the image forming apparatus 100 according to the embodiment, after the variation amount of the representative patch $P_{rep}$ measured at different points of time becomes equal to or smaller than the threshold Th, the colorimetry starting control unit 150 starts colorimetry of each patch 200 included in the test pattern using the colorimetric camera 20. Accordingly, the image forming apparatus 100 according to the embodiment can start colorimetry of each patch 200 included in the test pattern at an appropriate timing regardless of the print condition when the test pattern is printed.

The specific embodiment of the present invention has been described above in detail. However, the present invention is not limited to the above embodiment as it is. The embodiment can be variously changed or modified without departing from the gist of the invention.

For example, in the embodiment described above, the colorimetric object is assumed to be each patch 200 included in the test pattern printed on the printing medium P by the image forming apparatus 100. However, the embodiment is not limited thereto. The colorimetric object may be various colors included in an image printed by the image forming apparatus 100 using a color material.

In the embodiment described above, the RGB value is measured as the color information of the colorimetric object to determine whether to start colorimetry of the colorimetric object. However, the embodiment is not limited thereto, and various color information can be used. For example, the colorimetric value of the representative patch $P_{rep}$ included in the test pattern may be measured to determine whether to start colorimetry of each patch 200 included in the test pattern based on a variation amount of the colorimetric value.

In the embodiment described above, the measurement of the color information to determine whether to start colorimetry of the colorimetric object and the colorimetry of the colorimetric object are both performed using the colorimetric camera 20. However, the embodiment is not limited thereto. The color information of the colorimetric object may be measured using a device different from the colorimetric camera 20 (colorimeter) that performs colorimetry of the colorimetric object.

In the embodiment described above, the specific example of the colorimetric method for the patch 200 is exemplified. However, the colorimetric method for the patch 200 is not limited thereto. For example, the colorimetric value of the patch 200 may be calculated using a method disclosed in Japanese Patent Application Laid-open No. 2012-63270 instead of the method described above.

First Modification

Next, a modification of the processing performed by the colorimetry starting control unit 150 implemented as a function of the CPU 101 will be described.

Figure 22:
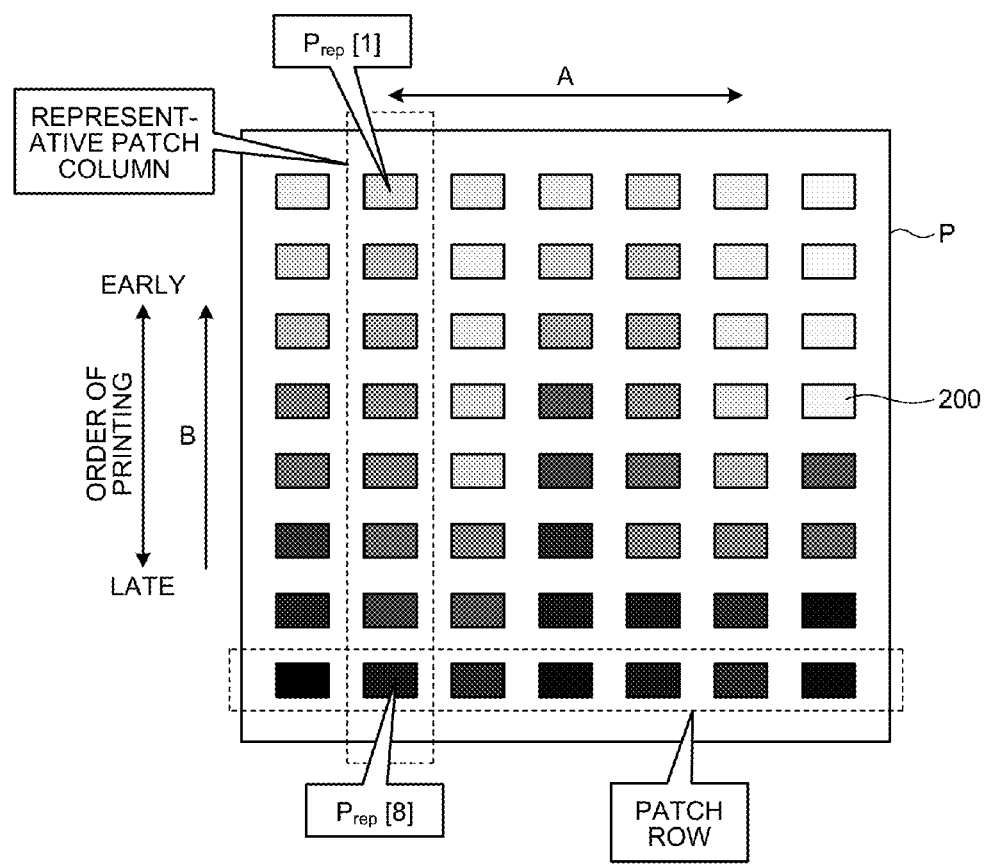
FIG. 22 is a diagram illustrating an example of a test pattern used in a first modification.

FIG. 22 is a diagram illustrating an example of a test pattern used in the first modification. As illustrated in FIG. 22, the test pattern used in the first modification includes a plurality of patch rows (eight rows in FIG. 22) arranged along a sub-scanning direction B, each of which includes a predetermined number of the patches 200 (seven patches 200 in FIG. 22) arranged along the main-scanning direction A. In the test pattern, the patches 200 for which drying time is relatively long are arranged in patch rows that are printed earlier in the order of printing, and the patches 200 for which drying time is relatively short are arranged in patch rows that are printed later in the order of printing. In a single patch row in which the order of printing is the same, the patch 200 for which the drying time is longest is determined as the representative patch $P_{rep}$ in advance. That is, the patch for which the drying time is longest among the patches 200 in each patch row is determined as the representative patch $P_{rep}$, for each patch row included in the test pattern. In the following, assuming that the test pattern includes eight patch rows, the representative patches $P_{rep}$ of the respective patch rows are denoted by $P_{rep}[1]$, $P_{rep}[2]$, ..., and $P_{rep}[8]$ in order from the representative patch $P_{rep}$ in the patch row that is the first in the order of printing.

In the first modification, the colorimetry starting control unit 150 performs processing as described below to control the timing for starting colorimetry of the patches 200 included in each patch row, for each patch row included in the test pattern illustrated in FIG. 22.

The colorimetry starting control unit 150 is called when the printing of the test pattern is finished, and moves the colorimetric camera 20 to a position opposite to the representative patch $P_{rep}[8]$ in the eighth patch row that is the last in the order of printing.

Subsequently, the colorimetry starting control unit 150 measures the RGB value (color information) of the representative patch $P_{rep}[8]$ by using the colorimetric camera 20, and holds the measurement result. Thereafter, the colorimetry starting control unit 150 waits for a predetermined time (t seconds). When t seconds elapse, the colorimetry starting control unit 150 measures the RGB value of the representative patch $P_{rep}[8]$ again by using the colorimetric camera 20. The colorimetry starting control unit 150 then obtains a variation amount of the RGB value of the representative patch $P_{rep}[8]$ from a difference between a newly obtained measurement result and the measurement result obtained t seconds before, and determines whether the variation amount is equal to or smaller than a predetermined threshold Th.

Herein, for example, the variation amount of the RGB value of the representative patch $P_{rep}[8]$ may be a change amount of a luminance value of a channel in which the difference in the measurement results is the largest among the channels of RGB, may be a change amount of a YUV value converted from the RGB value, may be a mixed value obtained by adding the measurement values of all of the channels of RGB, or may be an average value of the measurement values of all of the channels of RGB. As the threshold Th for the variation amount, for example, it is preferable to set a value in advance by which it is assumed that there is no variation in the RGB value with consideration of a measurement error.

When the variation amount of the RGB value of the representative patch $P_{rep}[8]$ exceeds the threshold Th, the colorimetry starting control unit 150 holds the measurement result obtained at the point of time, and measures the RGB value of the representative patch $P_{rep}[8]$ again after lapse of t seconds. The colorimetry starting control unit 150 then obtains the variation amount of the RGB value of the representative patch $P_{rep}[8]$ again by using the same method as described above, and determines whether the variation amount is equal to or smaller than the threshold Th again.

The colorimetry starting control unit 150 repeats the processes described above until the variation amount of the RGB value of the representative patch $P_{rep}[8]$ becomes equal to or smaller than the threshold Th. After the variation amount of the RGB value of the representative patch $P_{rep}[8]$ becomes equal to or smaller than the threshold Th, the colorimetry starting control unit 150 outputs a control command to start colorimetry of each patch 200 included in the eighth patch row that is the last in the order of printing.

In response to the control command from the colorimetry starting control unit 150, colorimetry of each patch 200 included in the eighth patch row is started by using the colorimetric camera 20. When colorimetry is started, the colorimetric camera 20 successively moves to a position opposite to each patch 200 included in the eighth patch row and captures an image of each patch 200. Then, the colorimetric value of each patch 200 is calculated from the RGB value of each patch 200 obtained by image capturing. In this case, the RGB value of the representative patch $P_{rep}[8]$ is already acquired, so that imaging of the representative patch $P_{rep}[8]$ can be omitted.

Thereafter, when the colorimetry of each patch 200 included in the eighth patch row that is the last in the order of printing is finished, the printing medium P on which the test pattern is printed is conveyed by the amount of conveyance corresponding to a space between the patch rows in a direction opposite to a printing direction of the test pattern. Then, the colorimetry starting control unit 150 moves the colorimetric camera 20 to a position opposite to the representative patch $P_{rep}[7]$ in the seventh patch row that is the second last in the order of printing.

Subsequently, the colorimetry starting control unit 150 measures the RGB value of the representative patch $P_{rep}[7]$ at every t seconds by using the colorimetric camera 20 in the same manner as the processing on the representative patch $P_{rep}[8]$, and determines whether the variation amount of the RGB value of the representative patch $P_{rep}[7]$ is equal to or smaller than a predetermined threshold Th. After the variation amount of the RGB value of the representative patch $P_{rep}[7]$ becomes equal to or smaller than the threshold Th, the colorimetry starting control unit 150 starts colorimetry of each patch 200 included in the seventh patch row. When the colorimetry of each patch 200 included in the seventh patch row is finished, the printing medium P on which the test pattern is printed is conveyed in the same manner as described above. Subsequently, the same processing as described above is repeated on the sixth patch row to the first patch row. When the colorimetry of each patch 200 included in the first patch row is finished, the colorimetry is completed.

Figure 23:
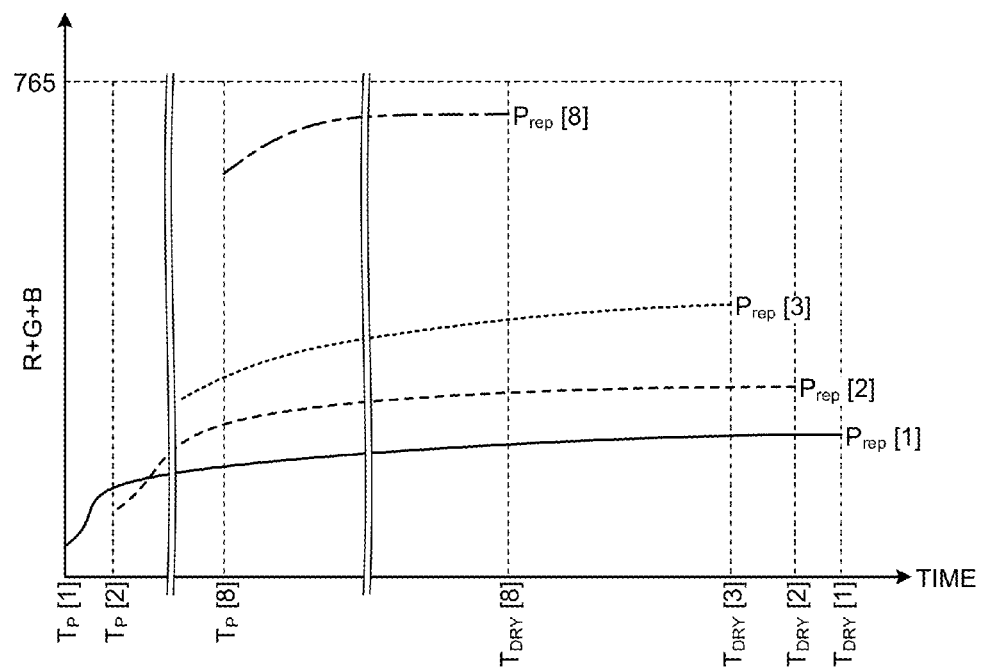
FIG. 23 is a diagram illustrating a temporal change in an RGB measurement result of the representative patch.

FIG. 23 is a diagram illustrating a temporal change in an RGB measurement result of the representative patch $P_{rep}$. In FIG. 23, a temporal change in a mixed value (R+G+B) that is obtained by adding the measurement values of all of the channels of RGB is illustrated for each of the representative patch $P_{rep}[1]$ in the first patch row, the representative patch $P_{rep}[2]$ in the second patch row, the representative patch $P_{rep}[3]$ in the third patch row, and the representative patch $P_{rep}[8]$ in the eighth patch row. In the drawing, $T_P[1]$ denotes a timing at which the representative patch $P_{rep}[1]$ is printed, $T_P[2]$ denotes a timing at which the representative patch $P_{rep}[2]$ is printed, and $T_P[8]$ denotes a timing at which the representative patch $P_{rep}[8]$ is printed. In the drawing, $T_{DRY}[8]$ denotes a timing at which ink of the representative patch $P_{rep}[8]$ is dried, $T_{DRY}[3]$ denotes a timing at which ink of the representative patch $P_{rep}[3]$ is dried, $T_P[2]$ denotes a timing at which ink of the representative patch $P_{rep}[2]$ is dried, and $T_P[1]$ denotes a timing at which ink of the representative patch $P_{rep}[1]$ is dried.

As illustrated in FIG. 23, the representative patches $P_{rep}$ of the respective patch rows are printed in order from the representative patch $P_{rep}[1]$ of the first patch row that is the first in the order of printing, and the representative patch $P_{rep}[8]$ of the eighth patch row that is the last in the order of printing is printed last. As described above, in the test pattern used in the first modification, the patches 200 for which drying time is relatively long are arranged in patch rows that are printed earlier in the order of printing and the patches 200 for which drying time is relatively short are arranged in patch rows that are printed later in the order of printing; therefore, the shorter the time taken until the ink of the representative patch $P_{rep}$ is dried, the larger the number of patch rows including the representative patch $P_{rep}$. Therefore, when a difference in the drying time between the patch rows is shorter than a printing time of a single patch row, as illustrated in FIG. 23, the ink of the representative patch $P_{rep}[8]$ of the eighth patch row that is the last in the order of printing is dried at the earliest time.

Figure 24:
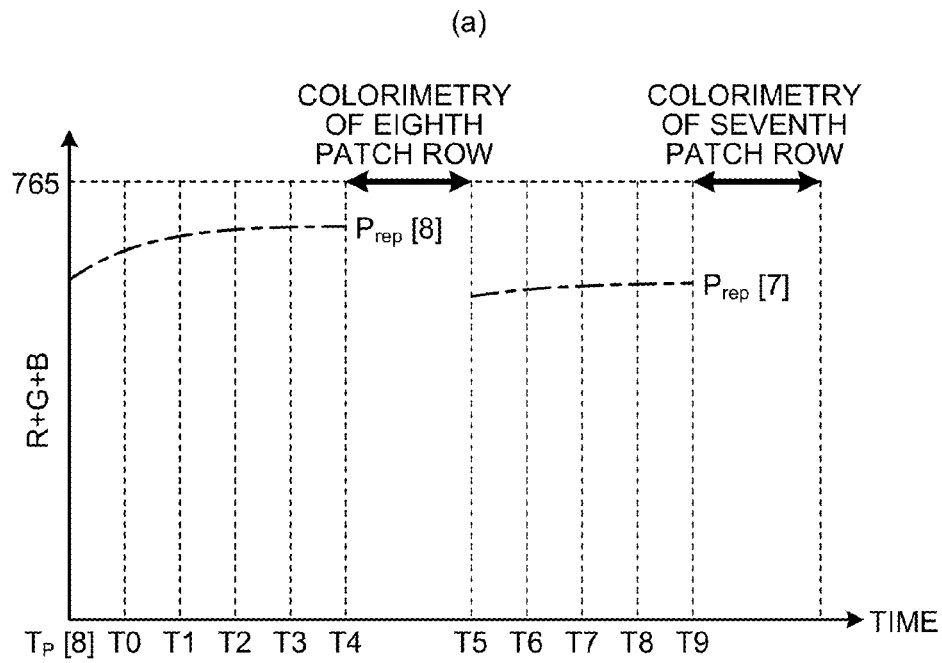
FIG. 24 illustrates processing performed by a colorimetry starting control unit according to the first modification.

FIG. 24 illustrates processing performed by the colorimetry starting control unit 150 according to the first modification. In FIG. 24, (a) illustrates a temporal change in the RGB measurement result (mixed value (R+G+B) obtained by adding the measurement values of all of the channels of RGB) of the representative patch $P_{rep}[8]$ and the representative patch $P_{rep}[7]$. In FIG. 24, (b) illustrates the RGB measurement result of the representative patch $P_{rep}[8]$ and the representative patch $P_{rep}[7]$ measured at each point of time T from the point of time $T_P[8]$ in (a) in FIG. 24.

When the test pattern is printed on the printing medium P, the colorimetry starting control unit 150 periodically measures the RGB value of the representative patch $P_{rep}[8]$, and determines whether the variation amount of the RGB value is equal to or smaller than the threshold Th. In the example illustrated in FIG. 24, the variation amount of the RGB value between the points of time T3 and T4 is equal to or smaller than the threshold Th. Accordingly, the colorimetry starting control unit 150 determines that the ink of the representative patch $P_{rep}[8]$ is dried at the point of time T4, and starts colorimetry of each patch 200 included in the eighth patch row.

When the colorimetry of each patch 200 included in the eighth patch row is finished, the colorimetry starting control unit 150 then periodically measures the RGB value of the representative patch $P_{rep}[7]$, and determines whether the variation amount of the RGB value is equal to or smaller than the threshold Th. In the example illustrated in FIG. 24, the variation amount of the RGB value between the points of time T8 and T9 is equal to or smaller than the threshold Th. Accordingly, the colorimetry starting control unit 150 determines that the ink of the representative patch $P_{rep}[7]$ is dried at the point of time T9, and starts colorimetry of each patch 200 included in the seventh patch row.

The colorimetry starting control unit 150 repeats the processing described above and controls the timing for starting colorimetry of each patch 200 included in each patch row, for each patch row included in the test pattern.

Figure 25:
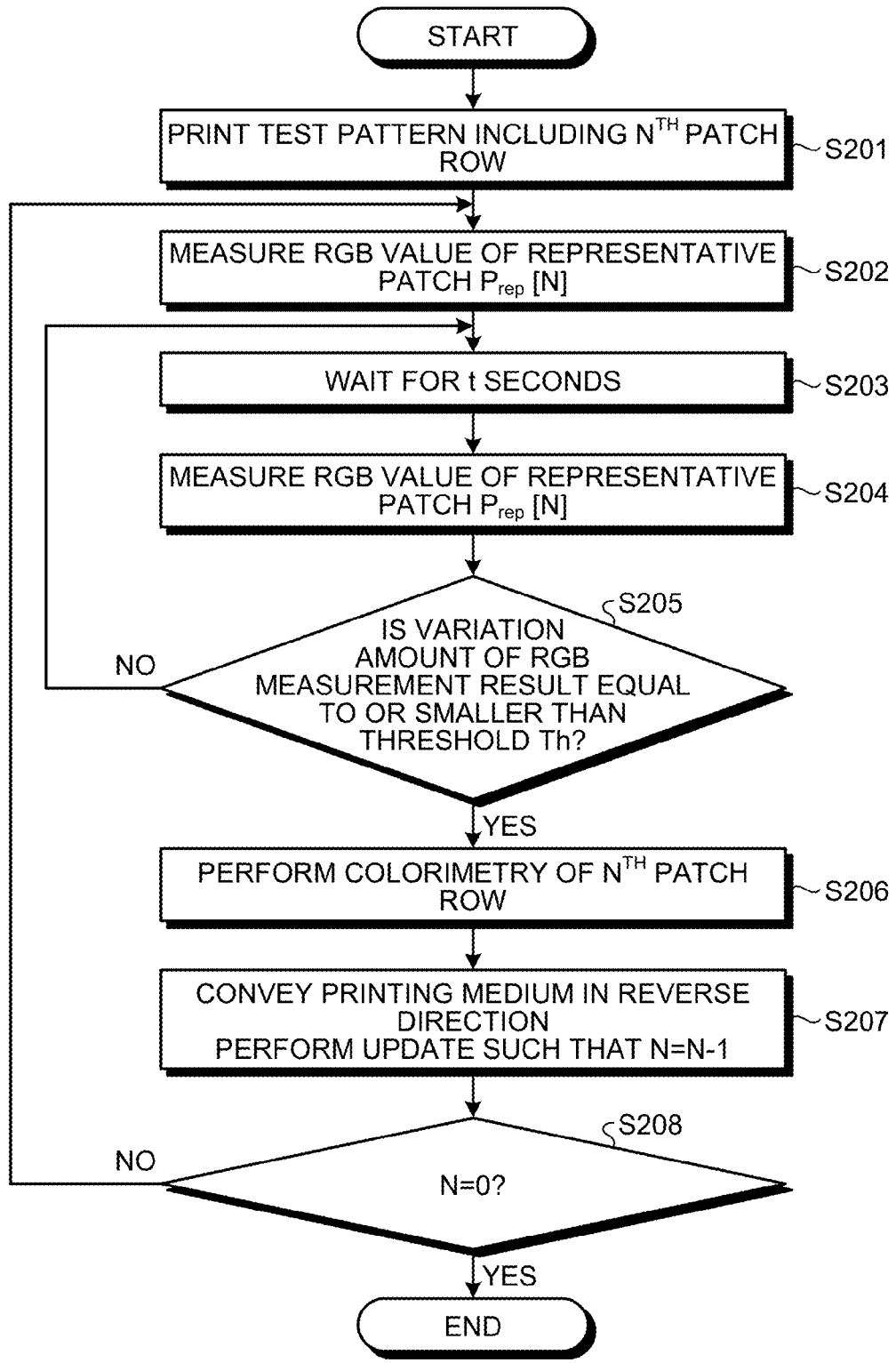
FIG. 25 is a flowchart illustrating a processing procedure according to the first modification.

FIG. 25 is a flowchart illustrating a processing procedure according to the first modification.

First, a test pattern including N patch rows (N is a natural number equal to or greater than two) is printed on the printing medium P (Step S201).

When the test pattern is printed, the colorimetry starting control unit 150 moves the colorimetric camera 20 to a position opposite to the N-th representative patch $P_{rep}[N]$, measures the RGB value of the representative patch $P_{rep}[N]$ by using the colorimetric camera 20, and holds the RGB measurement result (Step S202).

Thereafter, the colorimetry starting control unit 150 waits for t seconds (Step S203). When t seconds have elapsed, the colorimetry starting control unit 150 measures the RGB value of the representative patch $P_{rep}[N]$ again by using the colorimetric camera 20 (Step S204). The colorimetry starting control unit 150 then obtains a variation amount of the RGB measurement result from a difference between the RGB measurement result of the representative patch $P_{rep}[N]$ measured at Step S202 and the RGB measurement result measured at Step S204, and determines whether the variation amount of the RGB measurement result is equal to or smaller than the predetermined threshold Th (Step S205).

As a result of the determination at Step S205, if the variation amount of the RGB measurement result of the representative patch $P_{rep}[N]$ exceeds the threshold Th (No at Step S205), the processing returns to Step S203 and subsequent processing is repeated. On the other hand, as a result of the determination at Step S205, if the variation amount of the RGB measurement result of the representative patch $P_{rep}[N]$ is equal to or smaller than the threshold Th (Yes at Step S205), the colorimetry starting control unit 150 starts colorimetry of each patch 200 included in the N-th patch row (Step S206).

Thereafter, when the colorimetry of each patch 200 included in the N-th patch row is finished, the printing medium P on which the test pattern is printed is reversely conveyed (conveyed in the direction opposite to the printing direction) by the amount of conveyance corresponding to a space between the patch rows, and the value N is updated with a value N−1 (Step S207). Subsequently, whether N=0, that is, whether the colorimetry of each patch 200 in all of the patch rows is finished, is determined (Step S208). As a result of the determination at Step S208, if it is not the case that N=0 (No at Step S208), the processing returns to Step S202 subsequent processing is repeated. On the other hand, if it is the case that N=0 (Step S208: Yes), the series of processing ends.

Second Modification

In the embodiment and the first modification as described above, the RGB value of the representative patch $P_{rep}$ included in the test pattern printed on the printing medium P is measured at different points of time by using the colorimetric camera 20, and drying of the patch 200 included in the test pattern is determined based on whether the variation amount is equal to or smaller than the threshold Th. However, the drying determination method as described above may be effectively applied to a method of determining drying of an arbitrary image (hereinafter, referred to as an actual image), not limited to the test pattern including the patch 200, printed on the printing medium P.

For example, when ink is ejected to the printing medium P made of vinyl chloride or the like, it takes time until the ink on the printing medium P (that is, an image formed with the ink) is dried. Therefore, conventionally, a long drying standby time is set, and next processing, such as conveyance of the printing medium P, is performed after the set drying standby time elapses. However, the time taken until the ink is actually dried may depend on not only the type of the printing medium P but also the ejection amount of the ink or the like; therefore, it may be necessary to wait during the drying wait time set in advance even when the ink is actually dried, which may cause reduction in the productivity.

Therefore, in the second modification, the RGB value of a part (for example, a portion where the ejection amount of ink is large) of the actual image printed on the printing medium P is measured at different points of time by using the colorimetric camera 20 described above, and whether the actual image is dried is determined based on whether the variation amount is equal to or smaller than the threshold Th. In the second modification, it is assumed that the FPGA 110 (see FIG. 6) described above has a function of a determining unit that determines drying of the actual image.

Figure 26:
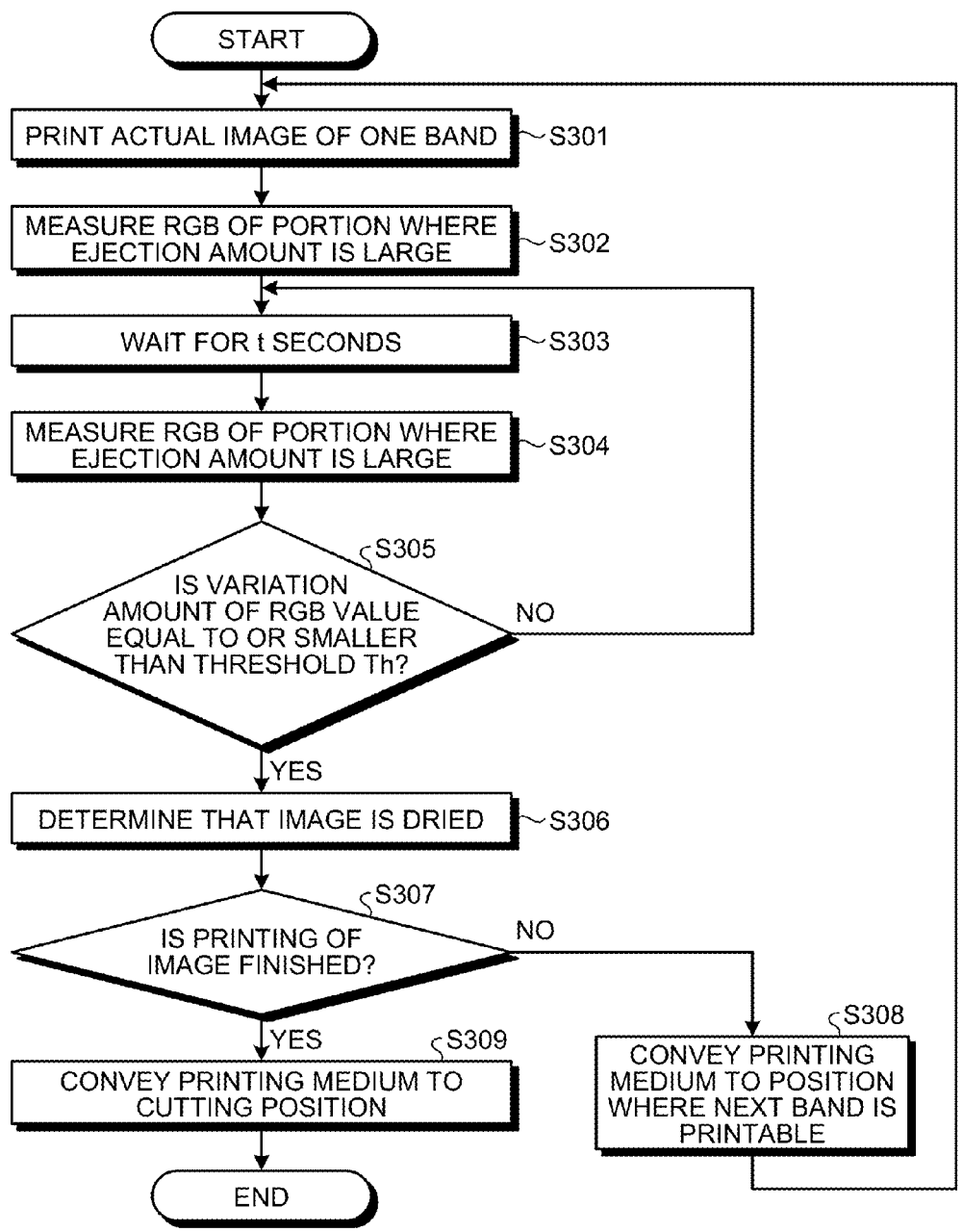
FIG. 26 is a flowchart illustrating a processing procedure according to a second modification.

FIG. 26 is a flowchart illustrating a processing procedure according to the second modification.

First, an actual image of one band is printed on the printing medium P (Step S301). The one band indicates a region along the sub-scanning direction, in which an image can be formed without conveying the printing medium P.

When the actual image of one band is printed, the FPGA 110 controls the main scanning motor 8 via the main scanning driver 105, and moves the colorimetric camera 20 to a portion where the ejection amount of the ink is largest within the printed actual image of one band. The FPGA 110 then measures the RGB value of the portion by using the colorimetric camera 20, and hold the measurement result (Step S302).

Thereafter, the FPGA 110 waits for t seconds (Step S303). When t seconds have elapsed, the FPGA 110 measures the RGB value of the portion where the ejection amount of the ink is largest within the printed actual image of one band again by using the colorimetric camera 20 (Step S304). The FPGA 110 then obtains a variation amount of the RGB value from a difference between the RGB value measured at Step S302 and the RGB value measured at Step S304, and determines whether the variation amount of the RGB value is equal to or smaller than the predetermined threshold Th (Step S305).

As a result of the determination at Step S305, if the variation amount of the RGB value exceeds the threshold Th (No at Step S305), the processing returns to Step S303 and subsequent processing is repeated. On the other hand, as a result of the determination at Step S305, if the variation amount of the RGB value is equal to or smaller than the threshold Th (Yes at Step S305), the FPGA 110 determines that the actual image of one band printed at Step S301 is dried (Step S306).

Thereafter, the FPGA 110 determines whether the printing of the entire actual image is finished (Step S307). If the printing is not finished (No at Step S307), the FPGA 110 controls the sub-scanning motor 12 via the sub-scanning driver 106 and conveys the printing medium P to a position where a next band is printable (Step S308). On the other hand, if the printing of the entire actual image is finished (Yes at Step S307), the FPGA 110 controls the sub-scanning motor 12 via the sub-scanning driver 106 and moves the printing medium P to a predetermined cutting position, for example (Step S309). The printing medium P conveyed to the predetermined cutting position is cut by a cutter or the like, and discharged to the outside of the image forming apparatus 100.

Figure 27:
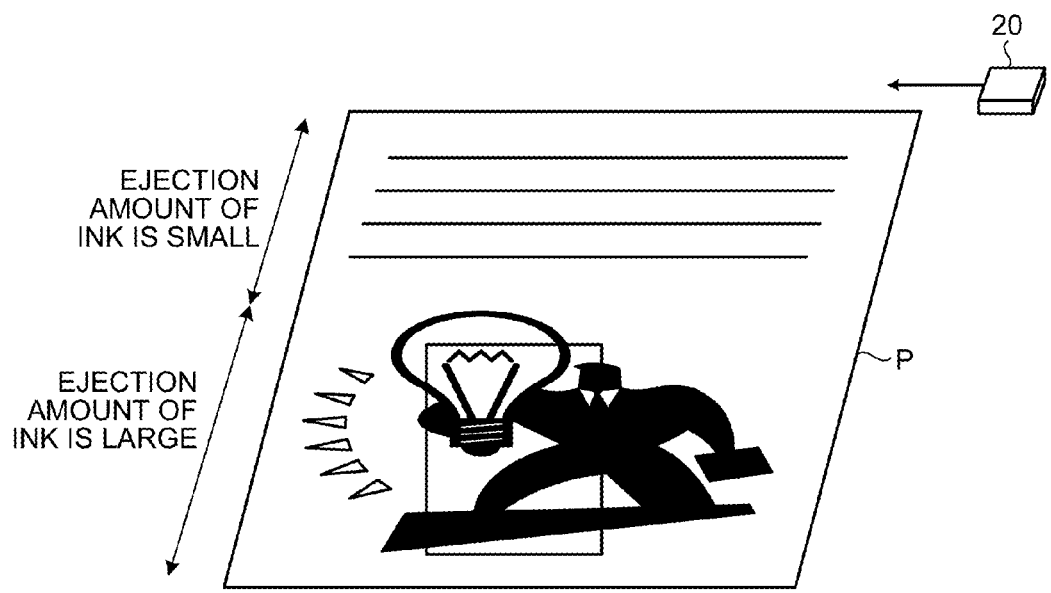
FIG. 27 is a diagram illustrating an example of an actual image.

As described above, in the second modification, whether the actual image of one band is dried is determined based on whether the variation amount of the RGB value of a part of the actual image of one band is equal to or smaller than the threshold Th. Therefore, as illustrated in FIG. 27 for example, when the actual image includes a region where the ejection amount of ink is large (a solid image or the like) and a region where the ejection amount of ink is small, it is possible to optimize the drying standby time in each of the regions, enabling to reduce unnecessary drying standby time. That is, it is possible to shorten the drying standby time for the region in which the ejection amount of the ink is small and which is dried rapidly, so that the productivity can be improved.

The processes performed after it is determined that the actual image is dried are not limited to the examples described above, and any processes that are performed after a wait for the actual image to dry are applicable. In the embodiment described above, colorimetry of the patch 200 is started after the variation amount of the RGB value of the representative patch $P_{rep}$ becomes equal to or smaller than the threshold Th. However, even in the embodiment described above, it may be possible to determine drying based on whether the variation amount of the RGB value the representative patch $P_{rep}$ is equal to or smaller than the threshold Th, and start colorimetry of the patch 200 after it is determined that "drying" is completed.

Third Modification

In the embodiment and modifications described above, a serial-head ink-jet printer is exemplified as an example of the image forming apparatus 100. However, the present invention is not limited to the example described above, and can be effectively applied to various types of image forming apparatuses that form images by ejecting ink to the printing medium P. For example, when the present invention is applied to a line-head ink-jet printer, a plurality of the colorimetric cameras 20 may be arranged in a direction perpendicular to the conveying direction of the printing medium P.

According to the embodiments described above, colorimetry of a colorimetric object can be started at an appropriate timing irrespective of print conditions for a colorimetric object.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An image forming apparatus comprising:
   a conveyor that conveys a recording medium;
   a printing unit that prints a plurality of patches using color material in a conveying direction;
   a color information acquiring unit that acquires color information of a representative patch that is a patch closest to an upstream side in the conveying direction among the plurality of patches; and
   a control unit that starts one of colorimetry using color information of the plurality of patches and color adjustment of the printing unit after a variation amount of color information of the representative patch measured at different points of time is equal to or smaller than a predetermined threshold.

2. The image forming apparatus according to claim 1, wherein an interval for measuring the color information of the representative patch is changed based on the variation amount of the color information.

3. A calibration method executed in an image forming apparatus, the calibration method comprising:
   conveying a recording medium;
   printing a plurality of patches using color material in a conveying direction;
   measuring color information of a representative patch at different points of time, the representative patch being a patch that is closest to an upstream side in the conveying direction among the plurality of patches;
   determining whether a variation amount of the color information of the representative patch is equal to or smaller than a predetermined threshold; and
   starting one of colorimetry using the color information and color adjustment of the image forming apparatus after the variation amount is equal to or smaller than the threshold.

* * * * *